US009418206B2

(12) United States Patent
Keefe et al.

(10) Patent No.: US 9,418,206 B2
(45) Date of Patent: Aug. 16, 2016

(54) METHOD AND APPARATUS FOR PREPARING A MEDICINAL SUBSTANCE

(71) Applicant: Codonics, Inc., Middleburg Heights, OH (US)

(72) Inventors: Gary Keefe, Brecksville, OH (US); Lawrence Srnka, Northfield Center, OH (US)

(73) Assignee: CODONICS, INC., Middleburg Heights, OH (US)

( * ) Notice: Subject to any disclaimer, the term of this patent is extended or adjusted under 35 U.S.C. 154(b) by 331 days.

(21) Appl. No.: 14/215,968

(22) Filed: Mar. 17, 2014

(65) Prior Publication Data

US 2014/0282197 A1    Sep. 18, 2014

Related U.S. Application Data

(60) Provisional application No. 61/798,798, filed on Mar. 15, 2013.

(51) Int. Cl.
*G06F 3/0484* (2013.01)
*G06F 19/00* (2011.01)

(52) U.S. Cl.
CPC .......... *G06F 19/326* (2013.01); *G06F 3/04842* (2013.01); *G06F 19/3456* (2013.01)

(58) Field of Classification Search
CPC .................................................. G06F 3/04842
USPC ....................................................... 715/771
See application file for complete search history.

(56) References Cited

U.S. PATENT DOCUMENTS

| 5,758,095 | A  | * | 5/1998  | Albaum   | G06F 19/322 |
|-----------|----|---|---------|----------|-------------|
|           |    |   |         |          | 705/2       |
| 5,845,255 | A  | * | 12/1998 | Mayaud   | G06F 19/3456 |
|           |    |   |         |          | 705/3       |
| 6,519,569 | B1 | * | 2/2003  | White    | A61M 5/142  |
|           |    |   |         |          | 604/151     |
| 8,065,161 | B2 | * | 11/2011 | Howard   | A61M 5/142  |
|           |    |   |         |          | 604/131     |
| 8,990,099 | B2 | * | 3/2015  | MacDonald | 705/2      |
| 9,037,479 | B1 | * | 5/2015  | MacDonald | G06Q 50/22 |
|           |    |   |         |          | 705/2       |
| 9,171,280 | B2 | * | 10/2015 | Gitchell | G06Q 10/087 |
| 9,262,585 | B2 | * | 2/2016  | Keefe    | G06F 19/36  |
| 2002/0042726 | A1 | * | 4/2002 | Mayaud | G06F 19/322 |
|           |    |   |         |          | 705/2       |
| 2006/0229557 | A1 | * | 10/2006 | Fathallah | G06F 19/3406 |
|           |    |   |         |          | 604/131     |

(Continued)

*Primary Examiner* — Reza Nabi
(74) *Attorney, Agent, or Firm* — Pearne & Gordon LLP

(57) ABSTRACT

Provided are a system and method for presenting information related to a drug dilution. A computer memory stores a drug database with a plurality of drug entries, each of which includes an identification and concentration of a drug stored in an originating container. A reader is operable to read a barcode associated with the drug identifier of the originating drug container and the concentration and/or dose and volume of the drug in the container. A user selects or enters a desired drug preparation that may include one or more preparations of the originating drug requested for administration to a patient. A computer processor interprets the concentrate signal, identifies the concentration of the originating drug based on content included in the drug database, and determines a recipe to be presented to the user for preparing the drug including any required dilutions.

13 Claims, 18 Drawing Sheets

(56) References Cited

U.S. PATENT DOCUMENTS

| | | | | |
|---|---|---|---|---|
| 2006/0265247 A1* | 11/2006 | Chaudhuri | G06F 19/327 | 705/2 |
| 2007/0088569 A1* | 4/2007 | Berkelhamer | G06F 19/328 | 705/2 |
| 2007/0125442 A1* | 6/2007 | Tribble | A61J 3/002 | 141/27 |
| 2007/0213598 A1* | 9/2007 | Howard | A61M 5/142 | 600/300 |
| 2008/0169045 A1* | 7/2008 | Tribble | B65B 59/00 | 141/1 |
| 2008/0314978 A1* | 12/2008 | Fedorko | G06Q 10/08 | 235/385 |
| 2010/0223069 A1* | 9/2010 | Kim | G06Q 10/00 | 705/2 |
| 2011/0093279 A1* | 4/2011 | Levine | G06F 19/326 | 705/2 |
| 2011/0267465 A1* | 11/2011 | Alexander | A61B 90/96 | 348/143 |
| 2012/0078819 A1* | 3/2012 | Norival | A61J 1/05 | 705/500 |
| 2013/0092727 A1* | 4/2013 | Edwards | B65C 11/0289 | 235/375 |
| 2013/0186950 A1* | 7/2013 | Keefe | G06F 19/326 | 235/375 |
| 2013/0191149 A1* | 7/2013 | Kolberg | G06F 19/3456 | 705/3 |
| 2013/0327822 A1* | 12/2013 | Keefe | G06F 17/40 | 235/375 |
| 2014/0282197 A1* | 9/2014 | Keefe | G06F 19/326 | 715/771 |
| 2015/0149198 A1* | 5/2015 | Edwards | G06F 19/326 | 705/2 |

* cited by examiner

```
         ┌ Drug Name:           Drug A ―52    ╱54  ╱56
         │ Container ID:        1111111111 ―64
         │ Drug Information:    Dose/Volume  = 100 mg/5 mL
         │                      Concentration = 20 mg/mL ―58
         │ Preparation Status:  Dilution Allowed ―66
         │ Preparation Method:  Dose/Volume
     A ⟨  Preparation Entries: ⎧ 100 mg/5  mL     Prep ID: 111111       69
         │                     ⎪ 100 mg/20 mL     Prep ID: 111112       ⎧
         │                  68⟨  100 mg/50 mL     Prep ID: 111113       [ x ] Non-standard
         │                     ⎪  50 mg/50 mL     Prep ID: 111114
         │                     ⎩ Other (mg/mL)    Prep ID: 111119 ―70
         │ Allowable Diluents:  Sterile Water ⎫
         └                      Normal Saline ⎭ 72

┌ Drug Name:           Drug B
         │ Container ID:        222222222
         │ Drug Information:    Dose/Volume  = 50 mg
         │                      Concentration = N/A
     B ⟨  Preparation Status:  Dilution Required
         │ Preparation Method:  Dose/Volume
         │ Preparation Entries: 50 mg/50 mL     Prep ID: 222221
         │                      10 mg/20 mL     Prep ID: 222222
         │ Allowable Diluents:  Sterile Water
         └                      Normal Saline ┌ Drug Name:           Drug C
         │ Container ID:        3333333333
         │ Drug Information:    Dose/Volume  = 5 mg/10 mL
         │                      Concentration = 0.5 mg/mL
         │ Preparation Status:  Dilution Allowed
     C ⟨  Preparation Method:  Diluted Concentration ―162
         │ Preparation Entries: 0.5 mg/mL       Prep ID: 333331
         │                      0.25 mg/mL      Prep ID: 333332
         │                      0.1 mg/mL       Prep ID: 333333
         │                      Other (mcg/mL)  Prep ID: 333339
         │ Allowable Diluents:  Sterile Water
         └                      Normal Saline
```

*FIG. 5*

Prescription — 90

Physician Order: 12-11111111 — 82
Physician Name: Dr. A. Adams — 84
Patient Name: John Q. Doe  
Patient ID: 1234567890 } 86

88 { Drug Name: Drug A  
Drug Preparation: Dose/Volume: 100 mg/50 mL — 54, 56  
Drug Administration: IV, Syringe Pump, 10 mg/hour

FIG. 6 — 80

User Interface - Pre-defined Drug Preparation Entries — 92

94 { Drug Name: Drug A  
Container ID: 1111111111  
Drug Information: Dose/Volume = 100 mg/5 mL  
Concentration = 20 mg/mL Select Preparation:  
68 { 100 mg/5 mL [ ]  
100 mg/20 mL [ ]  
100 mg/50 mL [ x ] — 96  
50 mg/50 mL [ ]  
Other (mg/mL) [ ] — 140

Select Diluent: Sterile Water [ ]  
Normal Saline [ x ] — 98

Prepared Concentration (calculated): 2 mg/mL

FIG. 7

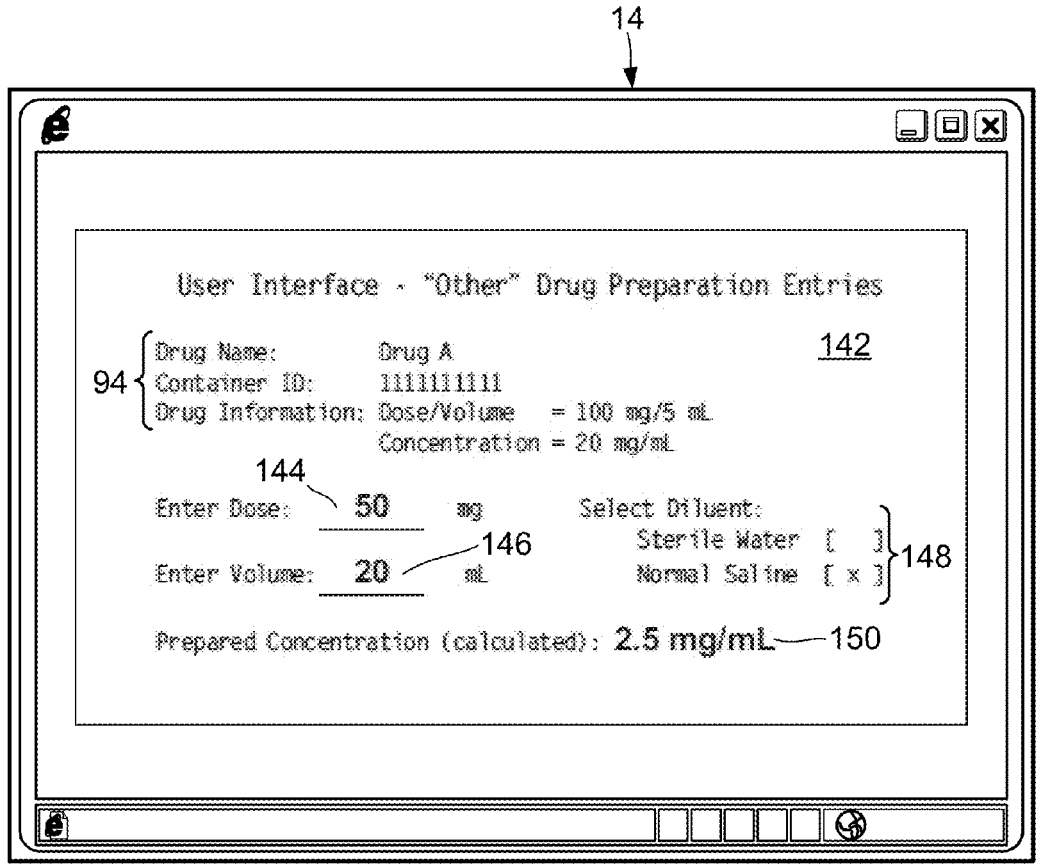

160
Prescription

Physician Order:    12-11111113
Physician Name:    Dr. A. Adams

Patient Name:    John Q. Doe
Patient ID:      1234567890

Drug Name:           Drug C
Drug Preparation:    Concentration: 0.25 mg/mL
Drug Administration: IV, Injection, Titration

Preparation Instructions
164

Drug Name:         Drug C
Drug Preparation:  Concentration = 0.25 mg/ml
                   Drug Dose     = N/A (Dilution by volume)

Step 1 (dilute):        Sterile            Final
  Drug C                Water              Preparation
  0.5 mg/mL                                0.25 mg/mL
  ─────────             ─────────          ─────────
  50% Volume    +       50% Volume    =    100% Volume

*FIG. 16*

METHOD AND APPARATUS FOR PREPARING A MEDICINAL SUBSTANCE

CROSS-REFERENCE TO RELATED APPLICATIONS

This application claims the benefit of U.S. Provisional Application No. 61/798,798, filed Mar. 15, 2013, which is incorporated in its entirety herein by reference.

BACKGROUND OF THE INVENTION

1. Field of the Invention

This application relates generally to a method and apparatus for preparing a drug or medicinal substance and, more specifically, to method and apparatus for selecting a specific preparation that may include reconstituting, diluting, measuring and mixing a drug or medicinal substance, and displaying preparation instructions and preparing a label including content related to the preparation and optionally encoding relevant preparation information as a machine-readable code.

2. Description of Related Art

It is common for drugs or other medicinal substances to require one or more preparation steps prior to being administered to patients at a healthcare facility. The preparation steps may include, but are not limited to: reconstitution; dilution; measuring a specific amount of a drug and/or substance; mixing multiple drugs and/or substances; packaging the final preparation in an appropriate container for delivery; and labeling the container with information related to the drugs and/or substances and/or preparation steps applied.

A specific drug preparation often begins with a prescription from a physician. This prescription may by issued verbally, or handwritten, or submitted using an electronic system.

A prescribing physician will often specify a dose and volume of the drug to be administered. To prepare a drug with the dose and volume prescribed, a clinician will select one or more originating drug containers having a proper starting concentration with the required amount of the specified drug. The number of containers, starting concentration and the amount of drug required from the containers may be specified as part of the drug recipe or preparation instructions that is associated with the specific preparation. In some cases, the contents of the originating drug containers must be diluted to achieve the prescribed dose and volume. A clinician preparing a diluted drug must select an appropriate diluent for diluting the drug, then calculate the volume of the drug and the volume of the diluent to be combined to achieve the desired dose and volume requested by the prescriber. This information can be included as part of the drug recipe to reduce the number a calculations a clinician must perform during the preparation process. The final drug preparation is commonly administered to a patient via a syringe or other delivery container.

Drugs are typically expensive, and are often administered in many different doses and volumes at a given healthcare facility depending on the specific needs of each patient. It is impractical to inventory, in a pharmacy, originating drug containers storing each of the different concentration variants that may be required.

Instead, a reasonable number vials storing the drug at different starting concentrations will commonly be kept in an inventory, from which the prescribed dose and volume and special concentrations are prepared. However, the dilution procedure described above for preparing a dilution is complex and time consuming. Additionally, the calculations of the drug volume and diluent volume to be combined to fulfill the prescription are prone to human error, thereby raising the possibility that a dilution with the improper dose and volume may be prepared.

BRIEF SUMMARY OF THE INVENTION

Accordingly, there is a need in the art for a method and apparatus for preparing a drug that may include reconstituting, diluting, measuring and mixing a drug or medicinal substance the drug, and generating a machine-printed label with a computer-readable code, on demand, for labeling the final prepared drug.

According to one aspect, the subject application involves a system for presenting information related to a drug dilution. The system includes a computer memory storing a drug database including a plurality of drug entries, each of which includes a drug identification that identifies a drug stored in a originating container and a concentration of the drug stored in the originating container. A reader is operable to read a barcode associated with the drug identifier of the originating drug container and at least one of; the concentration; or dose and volume of the drug in the container; and transmits a signal associated with concentration, dose and/or volume information. An input device presents a user with a user interface for selecting or entering a desired drug preparation that may include one or more preparations of the originating drug requested for administration to a patient. A computer processor is adapted to interpret the concentrate signal, identify the concentration of the originating drug based on content included in the drug database, and determine a recipe to be presented to the user for preparing the drug including any required dilutions.

According to another aspect, the subject application involves a system for presenting information related to a drug dilution. The system includes a computer-readable memory storing a drug database comprising a plurality of drug entries, each of which includes a drug identification that identifies a drug stored in a drug container, and a concentration of the drug stored in the drug container. A reader reads a computer-readable code associated with the drug identifier of the originating container and the concentrated drug in the container and transmits a concentrate signal. An input device presents a user with a user interface for selecting or entering a desired drug preparation of the concentrated drug requested for administration to a patient. A computer processor is also adapted to interpret the concentrate signal to identify the concentration of the originating drug based on content included in the drug database and utilize the desired drug preparation information entered by the user on the user interface to determine label content to be printed onto a label that is to be applied to a delivery container storing the desired dilution for administration to the patient. The label content comprises a second computer-readable code encoding information identifying the desired dilution, a diluent used to dilute the concentrated drug, and a total dose and total volume of the desired dilution.

The above summary presents a simplified summary in order to provide a basic understanding of some aspects of the systems and/or methods discussed herein. This summary is not an extensive overview of the systems and/or methods discussed herein. It is not intended to identify key/critical elements or to delineate the scope of such systems and/or methods. Its sole purpose is to present some concepts in a simplified form as a prelude to the more detailed description that is presented later.

BRIEF DESCRIPTION OF SEVERAL VIEWS OF THE DRAWING

The invention may take physical form in certain parts and arrangement of parts, embodiments of which will be described in detail in this specification and illustrated in the accompanying drawings which form a part hereof and wherein:

FIG. 5 shows an illustrative embodiment of drug entries A, B, C included in a formulary for Drug A, Drug B and Drug C, respectively, in the originating containers 50 of FIG. 4;

FIG. 6 shows an illustrative embodiment of a prescription issued by a prescribing physician with a prescribed total dose and total volume of Drug A to be administered to a patient;

FIG. 7 is a drug interface displayed by a computer terminal to a user;

FIG. 11 shows a corrected Other Dilution interface;

FIG. 12 shows a prescription that requires Drug B to be diluted to a dilution with a dose and volume of 20 mg/20 mL from a powder stored in an originating container with a total dose of 50 mg;

FIG. 15 shows another illustrative embodiment of a prescription requiring a dilution;

FIG. 16 shows another embodiment of a Preparation Instructions interface corresponding to the prescription of FIG. 15 displayed by a computer terminal;

DETAILED DESCRIPTION OF THE INVENTION

Figure 1:
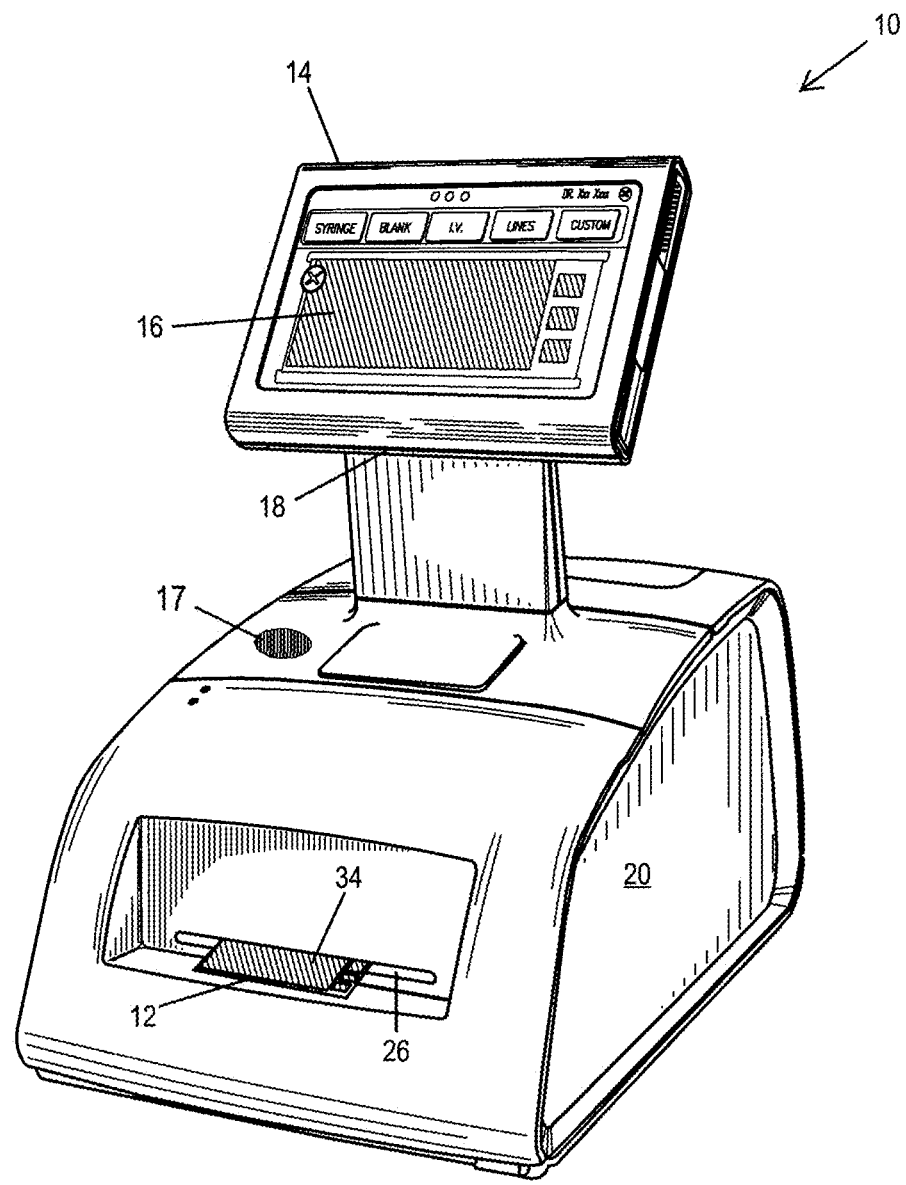
FIG. 1 is an illustrative embodiment of a stand-alone computer terminal to be utilized in the preparation of a medicinal substance and/or the printing labels identifying a medicinal substance.

Certain terminology is used herein for convenience only and is not to be taken as a limitation on the present invention. Relative language used herein is best understood with reference to the drawings, in which like numerals are used to identify like or similar items. Further, in the drawings, certain features may be shown in somewhat schematic form.

It is also to be noted that the phrase "at least one of", if used herein, followed by a plurality of members herein means one of the members, or a combination of more than one of the members. For example, the phrase "at least one of a first widget and a second widget" means in the present application: the first widget, the second widget, or the first widget and the second widget. Likewise, "at least one of a first widget, a second widget and a third widget" means in the present application: the first widget, the second widget, the third widget, the first widget and the second widget, the first widget and the third widget, the second widget and the third widget, or the first widget and the second widget and the third widget.

An illustrative embodiment of a computer terminal 10 is shown in FIG. 1, and includes a cabinet 20 supporting a touch-sensitive display 14 that can convert contact between a human operator and a region of the display's surface into an input signal. A printer 26 for printing label content 34 onto a label 12 can be incorporated into the cabinet 20, and a reader 18 that is operable to read a computer-readable code associated with a concentrated drug to be diluted is incorporated into the display 14. According to the illustrative embodiment the cabinet 20 including the printer 26 and the display 14 including the reader 18 collectively form the computer terminal 10 as an integrated unit. Although features such as the display 14 can be adjustable, and optionally separable from the cabinet 20, for example, the integrated unit is a so-called "all-in-one" computer terminal where each of the above components are packaged as a single, monolithic assembly. An example of such a computer terminal is described in U.S. patent application Ser. No. 13/274,184 to Edwards et al., which is incorporated in its entirety herein by reference.

Figure 2:
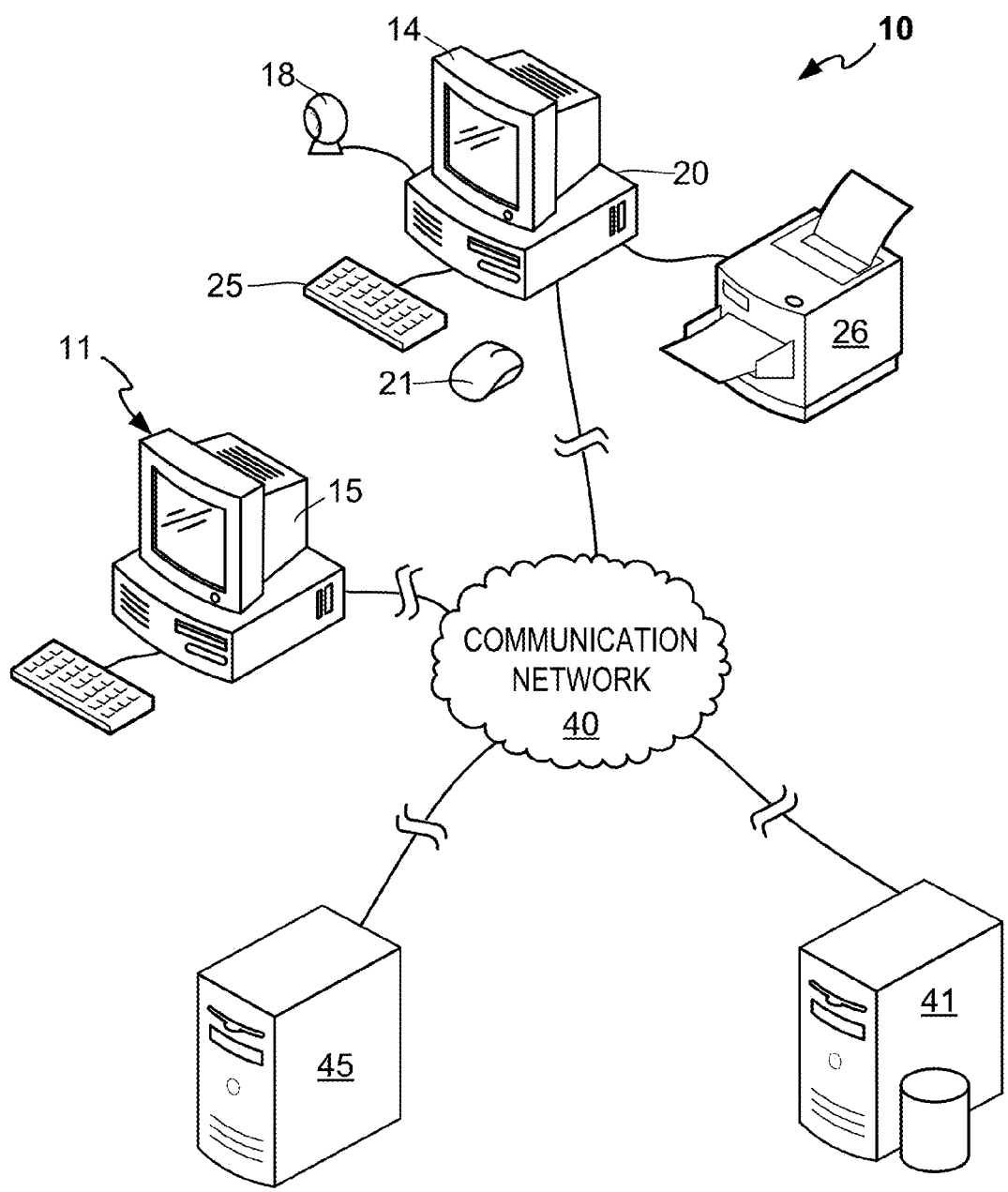
FIG. 2 is an illustrative embodiment of a networked computer system for preparing a medicinal substance and/or a label for a medicinal substance.

According to alternate embodiments, the computer terminal 10 can be configured as a component-based terminal as shown in FIG. 2, for example. As shown, the cabinet 20 can be embodied as a so-called desktop computer cabinet, housing components such as a processing component 22 (FIG. 3) such as a suitably programmed microprocessor and a memory component 24 such as a hard disk drive, for example, can be separate from the display 14, which can be touch-sensitive or non-touch-sensitive computer monitor. Communications between the cabinet 20 and display 14 can be established by a component, serial, DVI, HDMI, or other suitable cable extending between compatible communication ports provided the cabinet 20 and display 14, respectively. Likewise, a peripheral pointing device such as a mouse 21 or trackball, for example, and a computer keyboard 25 can be separate from, but operatively connected to communicate with the components housed by the cabinet and input user input such as commands and data. Rather than being incorporated into, or otherwise supported by a portion of the display 14, the reader 18 can be arranged as a peripheral device operatively connected to communicate with components within the housing 20 via a wired (e.g., USB, Ethernet, etc. . . . ) or wireless (e.g., 802.11, Bluetooth, etc. . . . ) communication channel. The printer 26 can also be arranged separate from, but operatively connected to the cabinet 20 to receive print jobs defining the label content 34 to be printed. Similar to the display 14, the printer 26 can be operatively connected to communicate with the components housed by the cabinet 20 over a USB cable, Ethernet cable, parallel cable, wireless communication channel, and the like.

Figure 3:
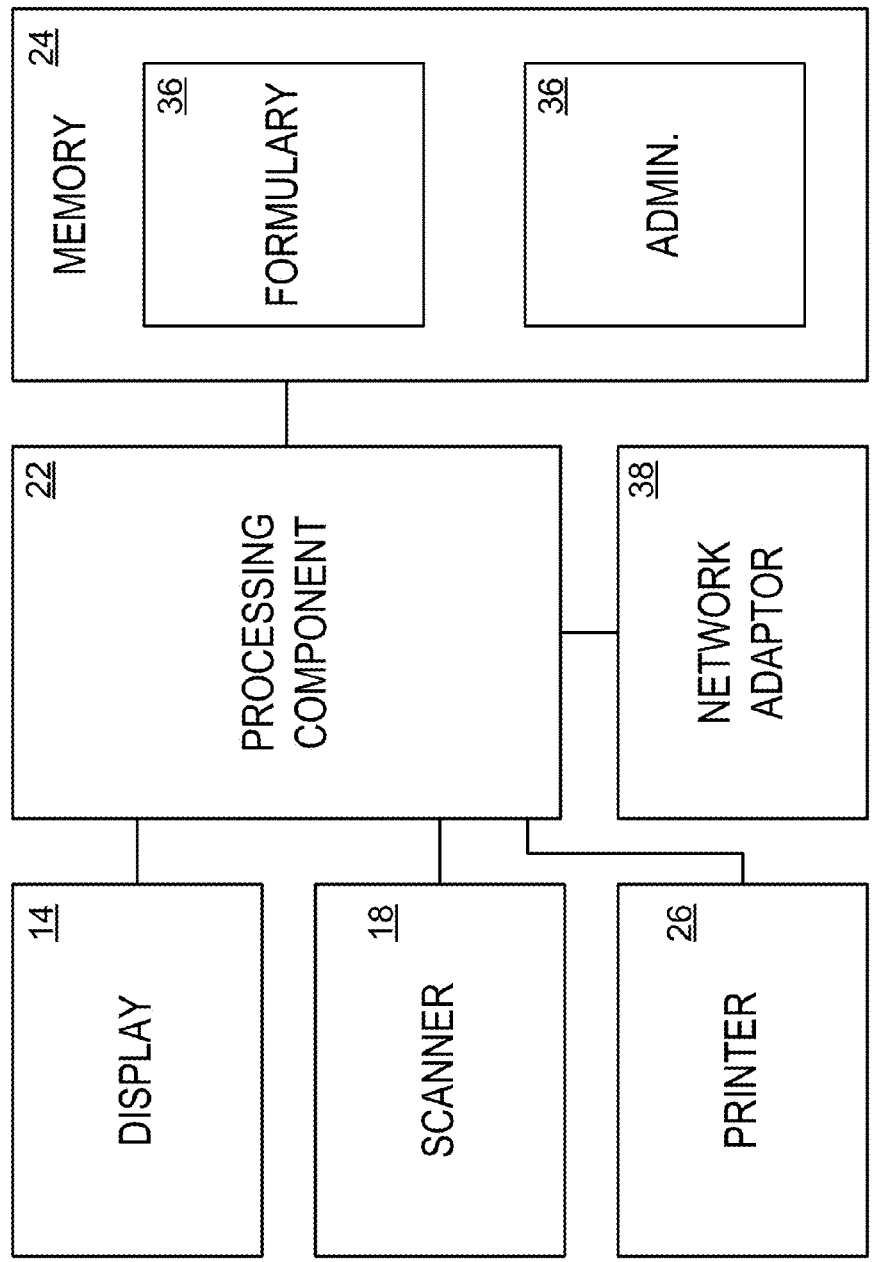
FIG. 3 is a block diagram schematically depicting components of an embodiment of a computer terminal.

Regardless of the implementation, the computer terminal 10 can include, as shown in FIG. 3, a memory component 24 that stores computer-executable instructions that are executable by a processing component 22. The processing component 22 includes a microprocessor or other suitable computer processor that can executed computer-executable instructions stored by the memory component 24 or received over a communication network by a network adaptor component 38. The components described herein can be formed from an arrangement of computer hardware such as ASICs, computer processors, programmable logic controllers and other circuitry; or a combination of computer hardware and computer-executable instructions. For example, the non-transitory, computer-readable memory 24 can include a hard disk drive ("HDD") and/or solid state drive ("SSD"), read-only memory ("ROM"), random access memory ("RAM"), optical disc, or any other suitable memory device, or any combination thereof. The computer-executed instructions, when executed by the computer processor 22, result in the performance of methods of instructing a user in preparing a dilution, and optionally generating a label for a diluted medicinal substance as described in detail below.

A BIOS 28 is provided to load the operating system and other such administrative instructions 30 stored in the memory 24 and manage hardware interface permissions of the computer terminal 10. The administrative instructions 30 can, when executed, control updates to a log documenting actions performed using the computer terminal 10, document the user or users who have input data for preparing a dilution or printing a label as described below, document other uses of the computer terminal, or any combination thereof.

In addition to the administrative instructions 30, the memory 24 also stores an updatable formulary 36 containing a database of medicinal substances that can be identified by the computer terminal 10 and select information for each medicinal-substance entry in the database. The formulary 36 can optionally be stored, updated and deleted from the memory 24 by the introduction of a so-called smart drive comprising a USB compatible flash memory to the computer terminal 10. When the smart drive is introduced to the computer terminal 10 according to such embodiments, it establishes the formulary 36 for that computer terminal 10. Illustrative examples of the select information that can be provided for the medicinal-substance entries includes, but is not limited to, an ID number such as a NDC code, UPC code, EAN code, or any other identifying data that can be used to relate a barcode or other computer-readable code read by the reader 18 to the medicinal-substance entries; a sound file that, when played, audibly announces the name of the medicinal substance identified in response to scanning a machine readable code; warning data; dilution data, or any combination thereof.

The display 14 can be touch-sensitive, receiving user input through contact between the user and the surface of the display 14. The display 14 is operable to display information such as the user interfaces described during the preparation of a dilution and/or printing of a label. Soft keys can also be displayed and, when touched by a user, input data and commands into the computer terminal 10. A virtual label 16 can also be displayed by the display 14 once sufficient information has been input to the computer terminal 10 to generate the label content 34 to be printed onto a label 12 with the printer 26, but before the label content 34 is printed. The user can review the label content 34 before it is printed and optionally enter confirmation to the computer terminal 10, confirming the accuracy of the label content 34 before that label content 34 is printed by the printer 26. The virtual label 16 is a computer-generated rendering of the label 12 that offers the user visual confirmation of the appearance of the physical label 12 including the label content 34 to be printed by the printer 26.

The reader 18 can include a barcode reader or radio-frequency identification ("RFID") tag reader, or any other device that reads a machine-readable code such as a barcode or RFID code, respectively, or any other machine-readable code without requiring contact between the computer terminal and the code, and optionally the user during entry of the code. According to alternate embodiments, the display 14 can be utilized by a user as the computer-input peripheral, and display soft keys that are selectable by the user to input information such as identification data, which can optionally include the data encoded by a barcode, a name of a medicinal substance, or other data identifying the medicinal substance to be diluted. According to yet alternate embodiments, a speaker 17 (FIG. 1) can optionally be provided to the cabinet 20, display 14, or any other portion of the computer terminal 10 to broadcast audible sounds such as warnings and/or prompts.

The network adaptor 38 can be operatively connected to communicate with the processing component 22 for translating signals received by the computer terminal 10 over a network 40 (FIG. 2) at a medical facility, such as that illustrated in FIG. 3. The network adaptor 38 can be compatible with any type of network communication. For example, the network adaptor 38 can include a hardwired, 10Base-T, 100Base-T, or 1000Base-T Ethernet interface with an RJ-45 socket, a coaxial cable interface, a fiber-optic interface, any format of wireless communication interface such as an antenna compatible with any of the 802.11 standards established by the IEEE, or any combination thereof. Embodiments including wireless network adaptors 38 can employ any desired securing protocol such as WEP, WPA and WPA2, for example, and other suitable security protocol. For embodiments including a network adaptor 38 compatible to communicate over a plurality of different network communication channels, both a hard-wired communication portion of the network adaptor 38 and a wireless communication portion of the network adaptor 38 can optionally be concurrently active. Thus, the computer terminal 10 can optionally communicate via both the hard-wired and wireless portions of the network adaptor 38 concurrently.

As used herein, a "system" can include the computer terminal 10, or at least each of the components of the computer terminal 10 described with reference to FIG. 3. Thus, an embodiment of the system utilized to perform the methods associated with preparing a dilution and optionally generating a label as described herein can include each of the components in FIG. 3 housed within, or at least coupled to the cabinet 20 of the computer terminal 10. For example, each of the components illustrated in FIG. 3 can be provided to the computer terminal 10 shown in FIG. 1. Data such as the formulary 36 and updates thereto can be received by the computer terminal 10 and stored locally in the memory 24. Such embodiments can perform the methods described herein independently of a status of the communication network 40 (i.e., the computer terminal 10 can optionally present the information for preparing a dilution and/or preparing a label for the dilution without communicating with a remote terminal over the communication network 40 as a prerequisite for presenting the user interfaces and/or printing the label 12). Thus, in the event there is a disruption of communications over the communication network 40, the computer terminal can be utilized to prepare a dilution and/or print a label 12 as described herein.

Alternate embodiments of the system, however, can include a portion of the components appearing in FIG. 3 distributed to be geographically separated from each other by the communication network 40, which can include a local area network ("LAN"), a wide area network ("WAN") such as the Internet for example, or a combination of a LAN and a WAN. For such illustrative embodiments, the memory component 24, for example, can be provided as part of a database server 41 (FIG. 2) or other remotely-located terminal storing the formulary 36 with the database of entries for the different medicinal substances. Retrieving information from or otherwise referencing information in the formulary 36 can require a communication between the computer terminal 10 and the database server 41 over the communication network 40. As another example of a distributed computational system, the processing component 22 utilized to execute computer executable instructions can be provided to the processing component 22 provided to a web server 45 (FIG. 2), for example, that is accessible by the computer terminal 10 over the communication network 40. Requests for preparing the dilution as described herein can be submitted over the communication network 40 to be processed by such a processing component 22 and the results returned to the computer terminal 10 to be presented to the user who entered the information contained in the request.

For the sake of brevity, and to clearly explain the methods of preparing dilution information, the system utilized herein to prepare the dilution will include the computer terminal 10 of FIG. 1, where the memory component 24 and the processing component 22 are locally provided to the computer terminal 10.

Figure 4:
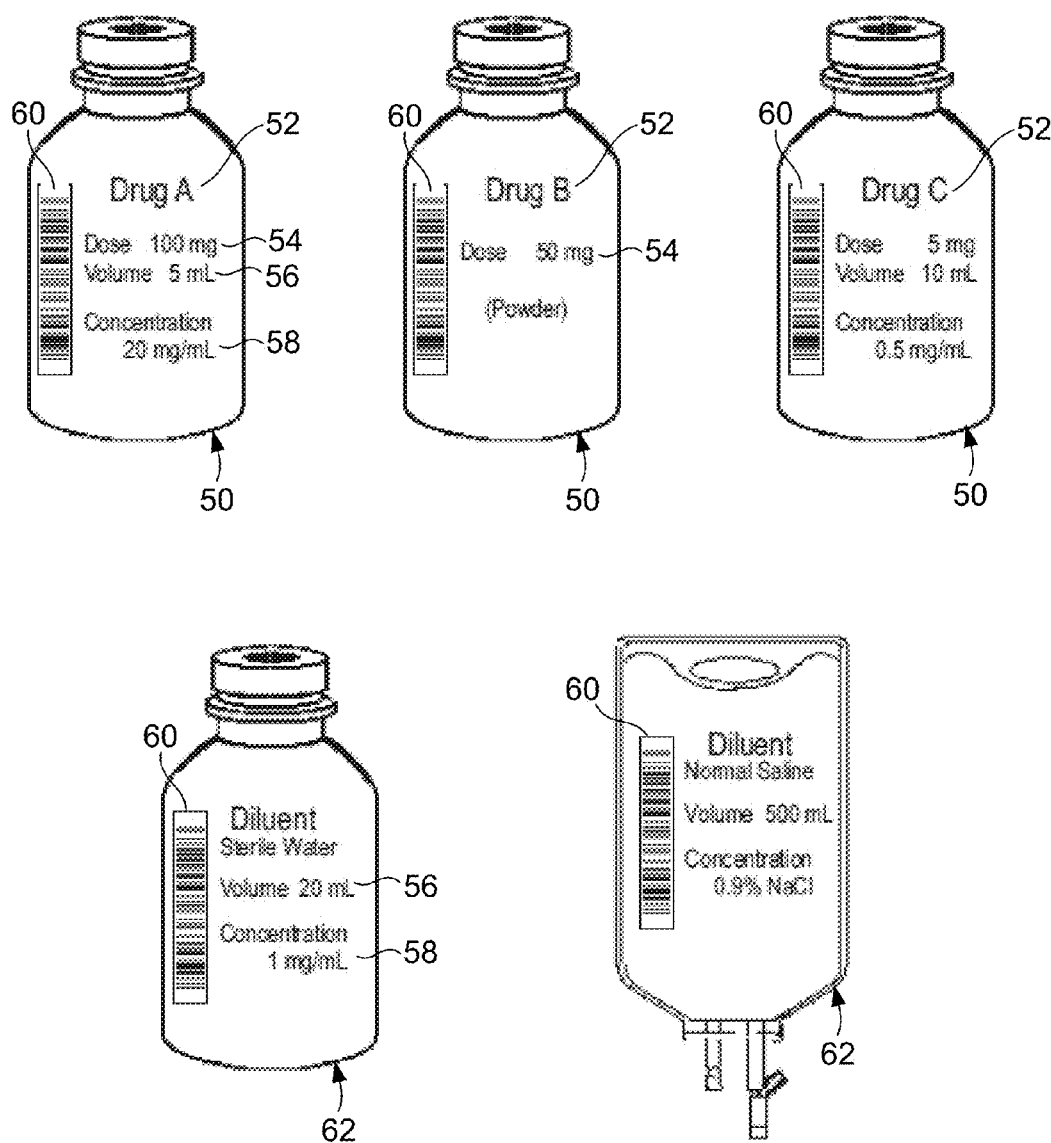
FIG. 4 shows illustrative embodiments of originating containers storing different concentrations of drugs (Drug A, Drug B, Drug C)

FIG. 4 shows illustrative embodiments of originating containers 50 storing different concentrated drugs (Drug A, Drug B, Drug C). The originating container 50 of each medicinal substance is commonly maintained in the inventory of a pharmacy of a medical facility such as a hospital, for example, and contains the concentrated drug from which drug preparations of the same concentration or drug preparations requiring dilutions of that drug are prepared to be introduced into a delivery container (e.g., a syringe) and administered to a patient. Each originating container 50 is labeled with label content that can include at least one of: the drug ID 52 identifying the medicinal substance by name, in human-readable alpha and/or numeric characters; total dose 54 of the medicinal substance stored therein when the originating container 50 is originally opened (i.e., before any of that medicinal substance is removed); total volume 56 of the medicinal substance therein when the originating container 50 is originally opened, and the concentration 58 of the medicinal substance therein when the originating container 50 is originally opened. The value of one or more of such information is encoded by, or at least linked to a machine-readable code applied to, printed on, or otherwise associated with the originating container 50. For the embodiment of FIG. 4, the machine-readable code is a barcode 60. Thus, when the barcode 60 is read, Drug A having the total dose 54, total volume 56 and concentration 58 associated with that barcode can be identified by the computer terminal 10.

The information used to label each medicinal substance can vary based at least in part on the state of the medicinal substance. For instance, Drug A is a liquid, so it is labeled with information such as the total dose 54, total volume 56 and concentration 58 of Drug A when the originating container 50 storing that drug is originally opened. In contrast, Drug B is a solid (e.g., powder), so the total dose 54 of Drug B in the originating container 50 when originally opened is included on the label of that originating container 50. Again, such information can be retrieved in response to scanning the barcode 60 provided to the originating container 50 for Drug B using the reader 18.

Similarly, diluent containers 62 storing substances for diluting the concentrated drugs can be provided with similar information. For example, a diluent containers 62 containing "Sterile Water" in FIG. 4 can be labeled with the originating total volume 56 and concentration 58 if appropriate, as well as a barcode that, when scanned by the reader 18, allows the computer terminal 10 to identify this information. The diluent container 62 storing "Normal Saline" in FIG. 4 is shown as an intravenous bag including an injection port 64 to which a quantity of the concentrated drug can be introduced to the Normal Saline, in situ. Thus, the introduced concentrated drug is diluted by the Normal Saline as it exits the diluent container 62. Additionally, the injection port 64 on the intravenous bag can be used to withdraw Normal Saline as required to dilute a drug being prepared in a syringe or other container.

FIG. 5 shows an illustrative embodiment of drug entries A, B, C included in the formulary 36 for Drug A, Drug B and Drug C, respectively, in the originating containers 50 of FIG. 4. The barcode 60 (FIG. 4) applied to (or otherwise associated with) a originating container 50 can be linked to the respective entry corresponding to the drug stored by the originating container 50. Thus, reading the barcode 60 for a originating container 50 can direct the computer terminal 10 to access the information contained in the corresponding drug entry of the formulary 36. Each drug entry A, B, C includes, depending on the state of the drug, at least one of the Drug ID 52, total dose 54, total volume 56 and concentration 58 of the respective drugs in their originating containers 50. Additionally, each entry can optionally include a Container ID 64, which is an identification number assigned to the originating container 50 to distinguish that originating container 50 from another originating container 50 of the same drug. The Container ID 64 can optionally be assigned internally, by the healthcare facility where the originating containers 50 are maintained in inventory for internal record-keeping purposes. Originating containers 50 with different Container IDs 64 can correspond to different batches, shipments or lot numbers of the drug, for example. Thus, a recall affecting one shipment of Drug A, for example, may not affect another shipment. The Container ID can be utilized to identify which originating containers 50 are affected by the recall and which originating containers 50 are not. Rather than discarding all originating containers 50 of Drug A, only those affected by the recall can be discarded or otherwise removed from the inventory of drugs available for administration to patients.

Each entry can also include a Preparation Status 66 indicating whether dilution of the corresponding drug is not allowed, allowed or required. Some drugs may be maintained in inventory at a concentration greater than the highest concentration allowed to be administered to a patient. For instance adult concentrations of drugs may be inventoried in a pharmacy for a pediatrics wing of a hospital. Entries for such drugs will include a Preparation Status 66 of "Dilution Required" as shown in the entry for Drug B in FIG. 5. Entries for drugs that can be, but are not necessarily required to be diluted can have a Preparation Status 66 of "Dilution Allowed" as shown in the entries for Drugs A and C in FIG. 5. Similarly, a drug with a Preparation Status 66 of "Dilution Not Allowed" or "Dilution Allowed" can be prepared at the same concentration as the originating container. In this case, the drug is commonly drawn from the originating container into a syringe without adding a diluent to reduce the concentration.

Each drug entry can also include one or more pre-defined preparations 68 of the drug corresponding to that entry. Pre-define preparations 68 can include dilutions and in some cases, all the preparations may be dilutions. Pre-defined preparations 68 can be added to the formulary 36 stored by the computer terminal 10 by an administrative user, also know as administrator, who has been granted the ability to modify the content of the formulary 36. The administrator can be granted privileges greater than, or at least different from the user who will utilize the computer terminal 10 to prepare a drug and/or prepare a label 12. For instance, the administrator can be a physician or pharmacist approved by the healthcare facility to edit the formulary 36, while a typical user who will prepare drugs using the computer terminal 10 may be a nurse. The pre-defined preparations 68 are those commonly administered to patients at the healthcare facility, and can be customized to add and/or remove preparation as desired. As explained in detail below, a user preparing a drug can be presented by a pre-populated menu of the pre-defined preparations 68 as selectable options when preparing a specified drug for administration to a patient.

If required, any pre-defined preparations 68 can be selected as a "Non-standard" preparation. In FIG. 5, a check box 69 corresponding to the "100 mg/50 mL" pre-defined preparation 68 has been selected by the administrator to identify it as being a Non-standard dilution. Non-standard dilutions can optionally be designated in the formulary 36 to identify a preparation that was added as a menu option at the request of a party, perhaps a specialist in a niche practice, for example, who will likely be the only party to select such a pre-defined preparation 68. Such a pre-defined preparation 68 may be necessary for pediatric patients, but not commonly administered to adult patients. A practice group including a single pediatric physician and many non-pediatric physicians may elect to designate the "100 mg/50 mL" pre-defined preparation 68 as Non-standard as only one of the many practitioners will commonly encounter such a dilution. Selection of a Non-standard pre-defined preparation 68 during the preparation of a drug or label 12 can optionally trigger a warning or alert indicating to the user that the Non-standard pre-defined preparation 68 has been selected. That user can input confirmation that the Non-standard pre-defined preparation 68 is indeed desired and proceed, or select a "Back" or "Cancel" option to select a different one of the pre-defined preparation 68 or manually enter another desired dilution. Confirmation that the Non-standard pre-defined preparation 68 is desired can be recorded in a log along with information identifying the party who entered such confirmation for auditing and record-keeping purposes. Labels printed with non-standard preparations can include additional information in the form of a human readable message stating the preparation is non-standard or by highlighting the non-standard information in a special color, font type or attribute, or text size. Formulary entries A, B, C can each independently include no Non-standard pre-defined preparations 68, at least one, or optionally a plurality of pre-defined preparations 68.

In addition to any pre-defined preparations 68, each entry can include optional "Other" entries 70. The Other entries 70 allows users of a menu-based system to prepare dilutions other than those that have been entered as pre-defined preparations 68 by an administrator. Thus, selection of the Other entries 70 allows a user to enter a custom preparation or dilution on terminal 10 that is not selectable from the set of pre-defined preparations 68 menu options. Just as for the selection of the Non-standard pre-defined preparation 68, a log can be updated with an entry identifying the Other entries 70 were entered and the user who prepared the drug with the Other entries 70 option.

For those entries in the formulary 36 designated as allowing or requiring dilution, one or more pre-defined diluents 72 can be established. Similar to the pre-defined preparations 68, the pre-defined diluents 72 can include one or more diluents that have been added by an administrator to the formulary entries before a time when the computer terminal 10 is being utilized to prepare the dilution and/or generate a label 12. Unlike the pre-defined preparations 68, however, users will be limited to selecting only one or more pre-defined diluents 72 that have been added to the formulary entries. The computer terminal 10 can optionally prevent users from specifying a diluent other than the pre-defined diluents 72, or at least prevent the user from proceeding with the dilution and/or label preparation process using the computer terminal 10 after specifying a diluent other than the pre-defined diluent(s) 72.

Although not shown in FIG. 5, one or more, and optionally each of the entries A, B, C can also include an instruction for preparing a drug, including instructions for preparing drugs including diluted drugs, corresponding to those entries. Any special precautions and/or instructions can be added to the entries to be presented to the user in response to initiating a dilution preparation process using the computer terminal 10. Examples of such instructions can include a warning about interactions with other drugs, abnormally short shelf lives of the preparations, dilutions, etc. . . . .

Figure 8:
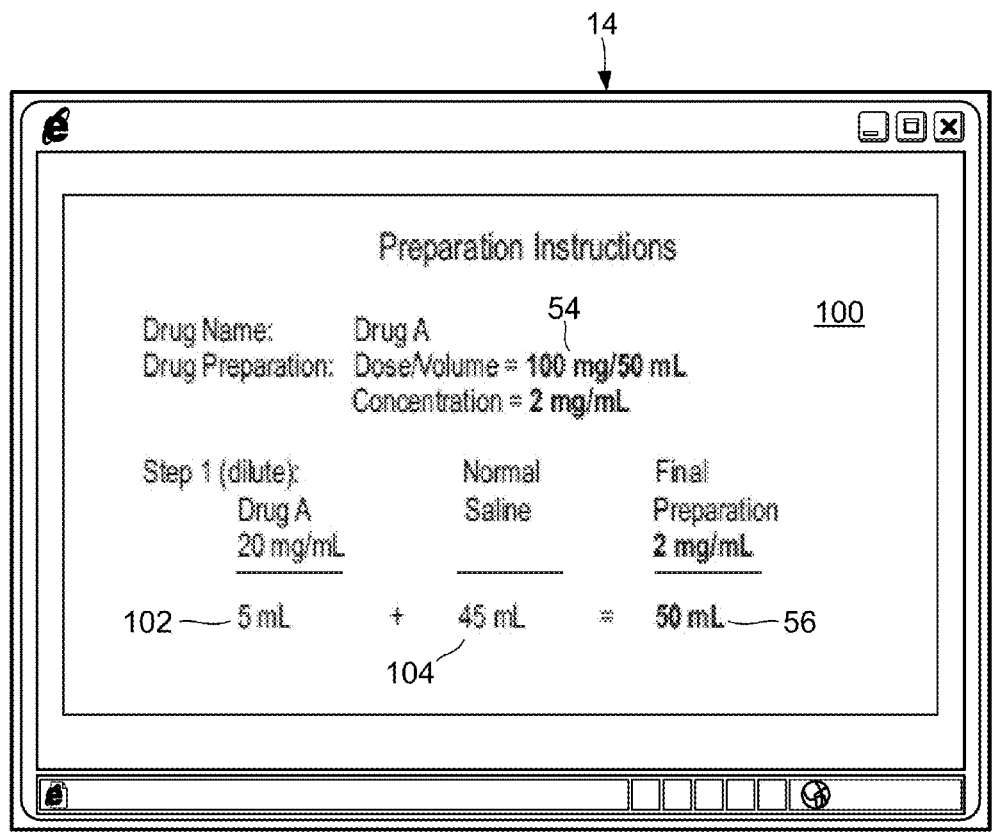
FIG. 8 shows a Preparation Instruction interface presenting instructions for a selected preparation to be displayed or otherwise presented by a computer terminal to a user.

According to one embodiment, instructions for a selected preparation to be displayed or otherwise presented by the computer terminal 10 as part of a Preparation Instructions interface 100, such as that shown in FIG. 8 and discussed below, can be assigned to entries in the formulary by a pharmacist or other authorized party. The instructions can be assigned and optionally stored in the formulary 36 in association with the respective drug to be included in the preparation. Such instructions can also optionally be assigned by the appropriate user through interactions with an Instruction Building interface 91 such as that illustrated in FIG. 20. The computer terminal 10, another computer terminal 11 (FIG. 2) included as part of a local embodiment of the communication network 40 implemented at a hospital or other healthcare facility, or a remote computer that is not operatively connected to communicate with other terminals and components of the local communication network. For the discussion below, however, the instructions are assigned using the other computer terminal 11, referred to hereinafter as a "pharmacy terminal 11", included in the network of FIG. 3. The pharmacy terminal 11 is operated by a pharmacist at a hospital pharmacy.

Figure 18:
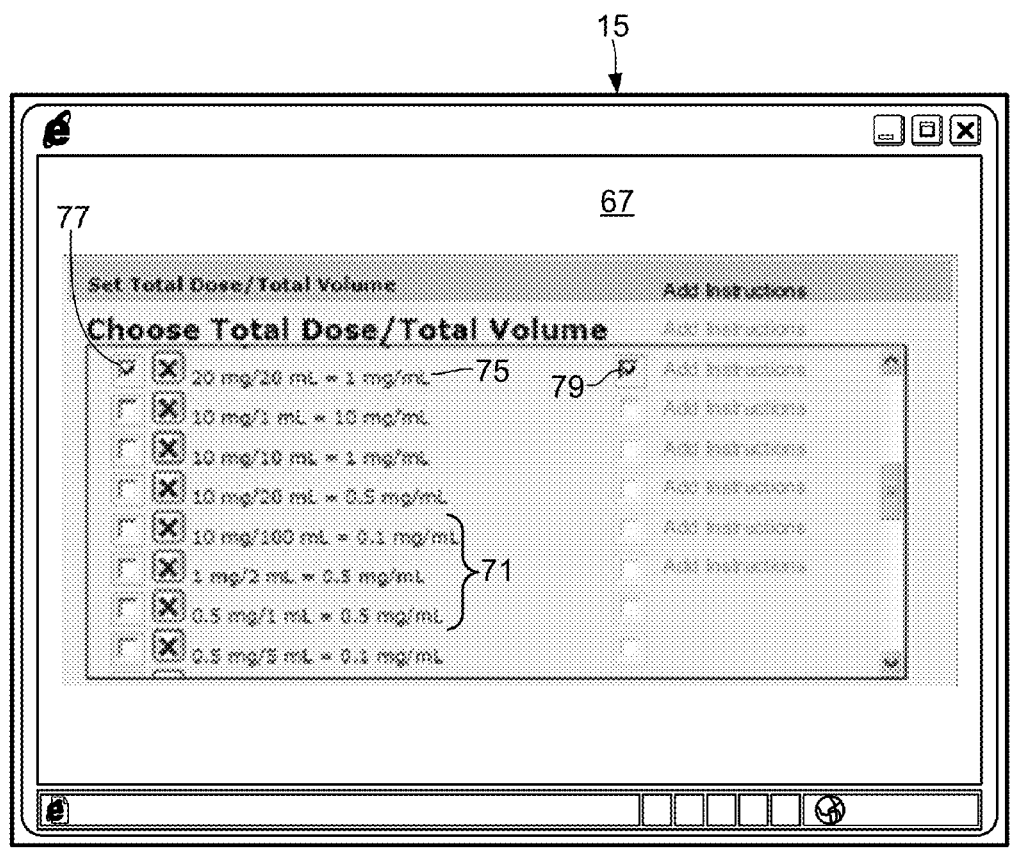
FIG. 18 shows an illustrative embodiment of a Total Dose/Volume selection interface displayed by a computer terminal in response to the entry of a drug to be used in a preparation at a different, pharmacy terminal.

In operation, the pharmacy terminal 11 executes computer-executable instructions stored by a hard disk drive or other non-transitory computer-readable medium to cause the display 15 provided to the pharmacy terminal 11 to display a Total Dose/Volume selection interface 67, such as that shown in FIG. 18 for example. The Total Dose/Volume selection interface 67 can optionally be displayed in response to the entry of a drug to be used in a preparation at the pharmacy terminal 11 by manual selection from a menu, manual entry via typed text entry, scanning a barcode or other computer-readable code provided to the originating container 50 storing that drug, etc. . . . Regardless of how the drug is selected at the pharmacy terminal 11, the Total Dose/Volume selection interface 67 presents a plurality of total doses/volumes 71 from which the pharmacist can choose the desired total dose/volume 75 by selecting the corresponding check box 77.

Figure 19:
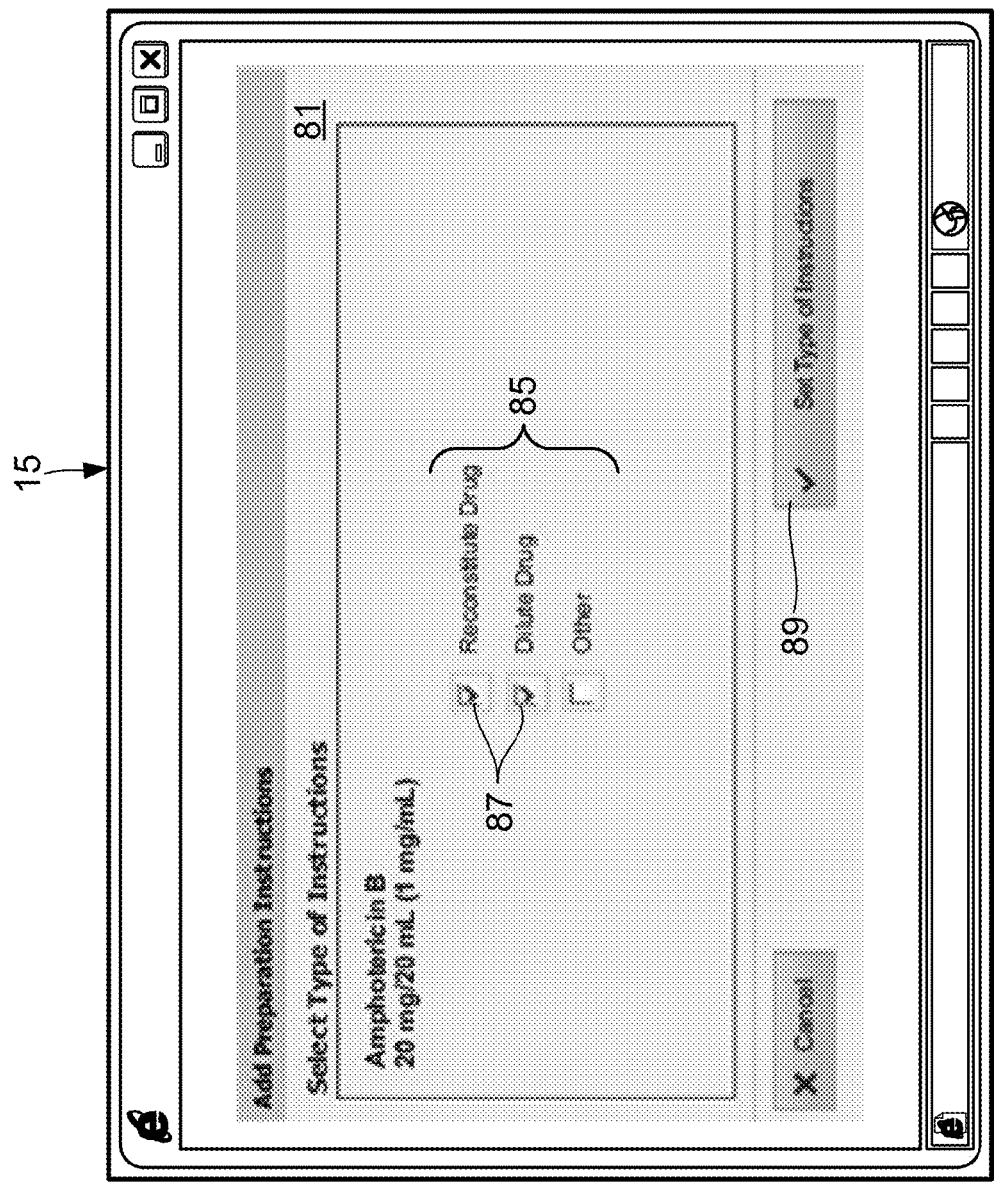
FIG. 19 shows an illustrative embodiment of a Type interface presented to a pharmacist by a pharmacy terminal including common types of preparation instructions prepared at a hospital or other healthcare facility.

The Total Dose/Volume selection interface 67 also gives the pharmacist the option to add a custom set of instructions that are to be displayed to a clinician by the computer terminal 10, for example, at a time when the clinician is preparing a syringe (or label 12 for a syringe) or other container with the preparation at the desired total dose/volume 75. If the "Add Instructions" check box 79 is selected, the Type interface 81 shown in FIG. 19 is presented to the pharmacist by the display 15 of the pharmacy terminal 11 as the method resumes. The Type interface 81 includes a list, pull-down menu, etc. . . . including the most common types of preparation instructions 85 prepared at a hospital or other healthcare facility. For the illustrative embodiment appearing in FIG. 19, instructions for reconstituting a drug, diluting a drug, and another, unspecified type of instruction set can be selected, although other possibilities can also be included without departing from the scope of the present disclosure.

Figure 20:
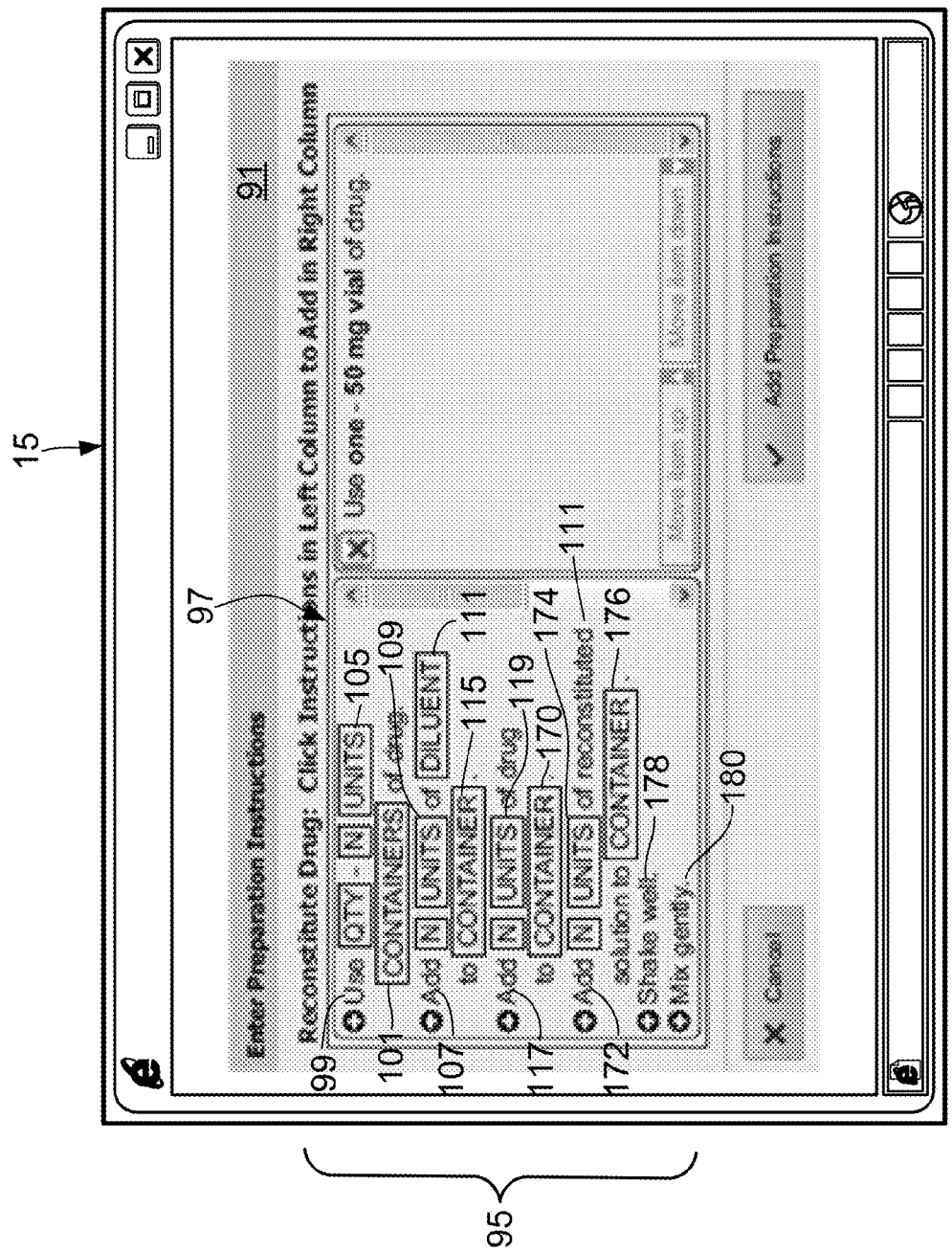
FIG. 20 shows an illustrative embodiment of an Instruction Building interface including instructions that are selectable to be assigned to an instruction set being created.

With the check box(es) 87 corresponding to the desired instruction type(s) selected, inputting a desire to continue via a "Set" button 89 in the Type interface 81 results in the Instruction Building interface 91 illustrated in FIG. 20 being displayed by the display 15 of the pharmacy terminal 11. The Instruction Building interface 91 includes a plurality of pre-existing instruction steps 95 that are commonly used in creating a preparation in a scrollable menu 97. For the non-exhaustive example shown in FIG. 20, the pre-existing instruction steps 95 in the menu 97 available for selection include, but are not limited to:

USE 99—selectable to indicate that the pharmacist is specifying the type 101 and size 105 of the originating container 50 from which the drug is to be withdrawn to create the preparation;

ADD 107—selectable to indicate that the pharmacist is specifying the quantity 109 and type 111 of diluent, reconstituting agent, etc. . . . to be combined with the drug, and the container 115 to which the diluent, reconstituting agent, etc. . . . is to be introduced;

ADD 117—selectable to indicate that the pharmacist is specifying the quantity 119 of the drug to be added, and the container 170 to which the drug is to be introduced for this particular preparation;

ADD 172—selectable to indicate that the pharmacist is specifying a quantity 174 of the type 111 (e.g., reconstituted, diluted, etc. . . . ) of drug preparation to be added to a container 176;

SHAKE WELL 178—selectable to include an instruction indicating that the person creating the preparation is to shake the container to vigorously mix the components;

MIX GENTLY 180—selectable to include an instruction indicating that the person creating the preparation is to shake the container in such a way to gently mix the components.

Figure 21:
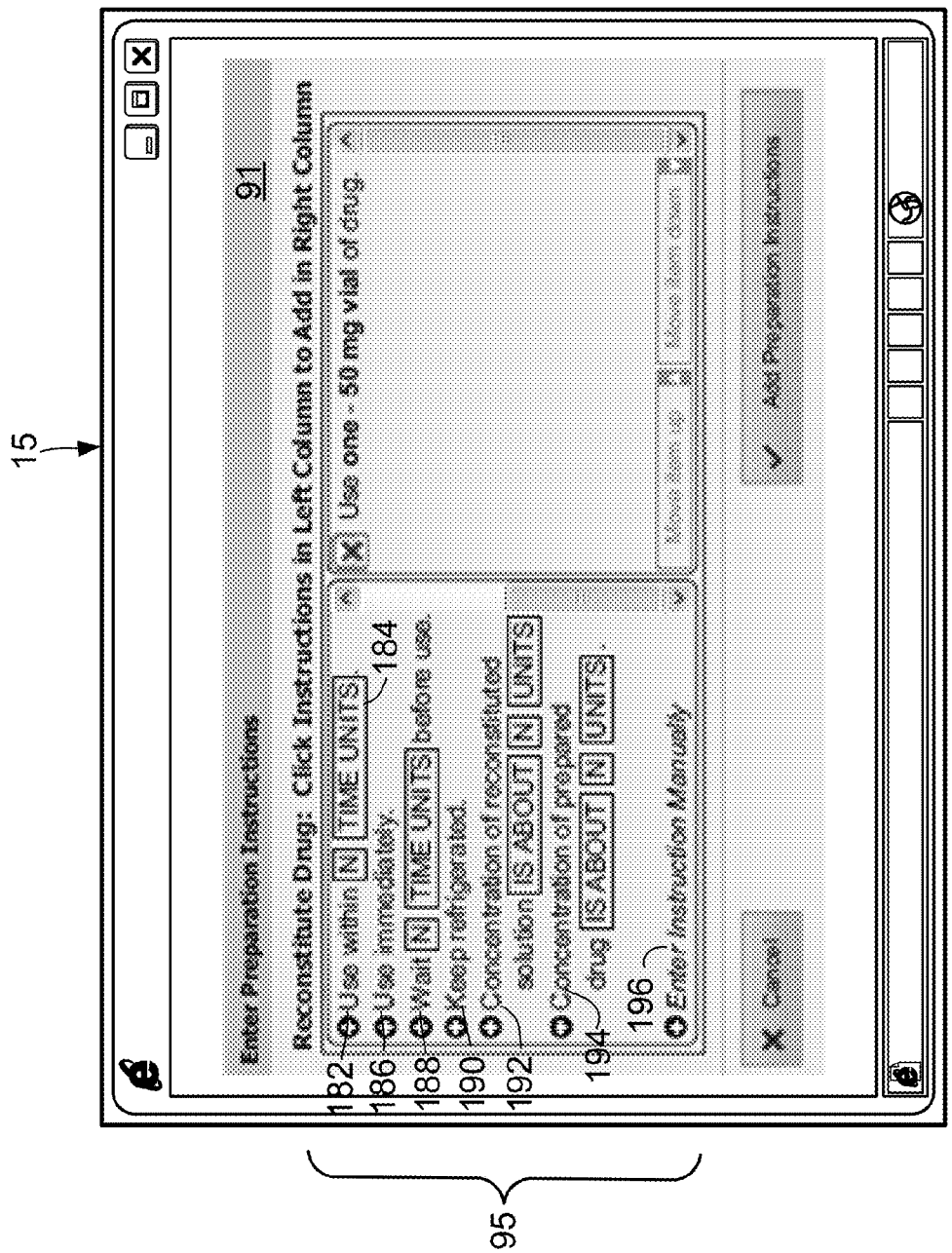
FIG. 21 shows an extension of the illustrative embodiment of the Instruction Building interface in FIG. 20.

As mentioned above, the menu 97 is scrollable to reveal additional pre-existing instruction steps 95 from which the preparer can choose, as shown in the bottom portion of the menu 97 in FIG. 21. The illustrative examples of such steps 95 shown in FIG. 21 include, USE WITHIN 182—selectable to include an instruction that the preparation, once completely prepared, should be used within a predetermined length of time 184 to be specified by the pharmacist;

USE IMMEDIATELY 186—selectable to include an instruction that the preparation, once completely prepared, should be used without delay;

WAIT 188—selectable to allow the pharmacist to input a predetermined length of time after the preparation is completely prepared that should be allowed to expire before the preparation is administered to a patient;

KEEP REFRIGERATED 190—selectable to allow the pharmacist to input an instruction that the preparation is to be kept in a refrigerated environment until a time when the preparation is to be administered;

CONCENTRATION 192—selectable to allow the pharmacist to input an approximate or specific concentration of the reconstituted solution (e.g., the solid drug dissolved, or at least suspended in a reconstituting agent);

CONCENTRATION 194—selectable to allow the pharmacist to input an approximate or specific concentration of the prepared drug (e.g., the liquid drug diluted by a diluent; and ENTER INSTRUCTION MANUALLY 196—selectable to allow the pharmacist to manually enter an instruction via keyed entry, etc. . . . .

Figure 22:
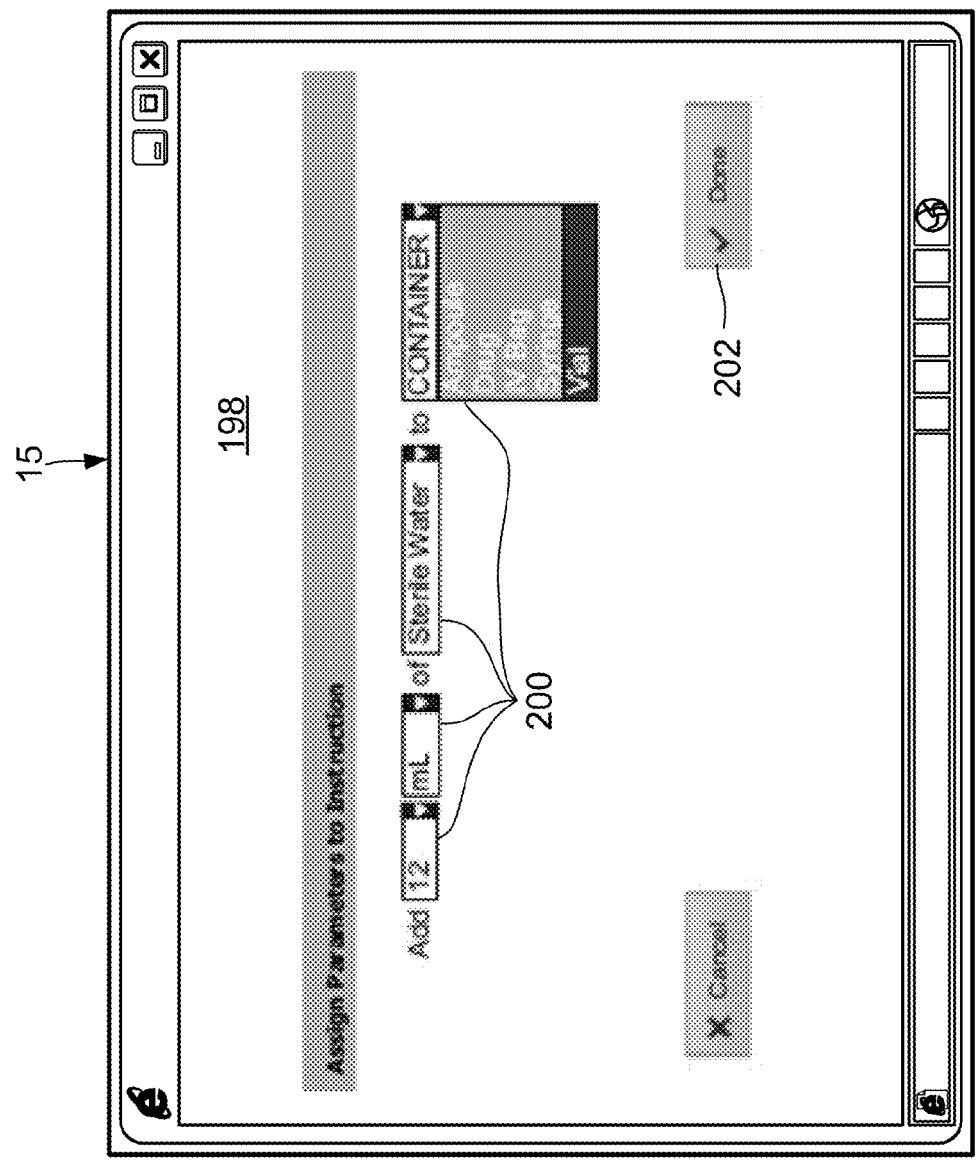
FIG. 22 shows an illustrative embodiment of a Parameter Interface that allows a user to specify a parameter, or a plurality of parameters for each instruction step selected from the Instruction Building interface.

A parameter, or a plurality of parameters can be specified by the pharmacist for each instruction steps 95 selected from the Instruction Building interface 91 utilizing a Parameter interface 198, an example of which is shown in FIG. 22. The Parameter interface 198 displayed in response to selection of an instruction step 95 allows the pharmacist to quantify the instruction step 95 selected. For example, the Parameter interface 198 shown in FIG. 22 is displayed in response to selection of the ADD 107 instruction step 95 in FIG. 20. This ADD 107 instruction step 95 in FIG. 20 requires the pharmacist to specify an integer "N", the "UNITS" of measurement, the name of the "DILUENT", and the "CONTAINER" to which the diluent is to be added. In the example shown in FIG. 22, the pharmacist has selected, from pull-down menus 200, "12" as the integer "N", "mL" as the "UNITS", "Sterile Water" as the "DILUENT", and the drug vial (e.g., the originating container 50) as the "CONTAINER".

Figure 23:
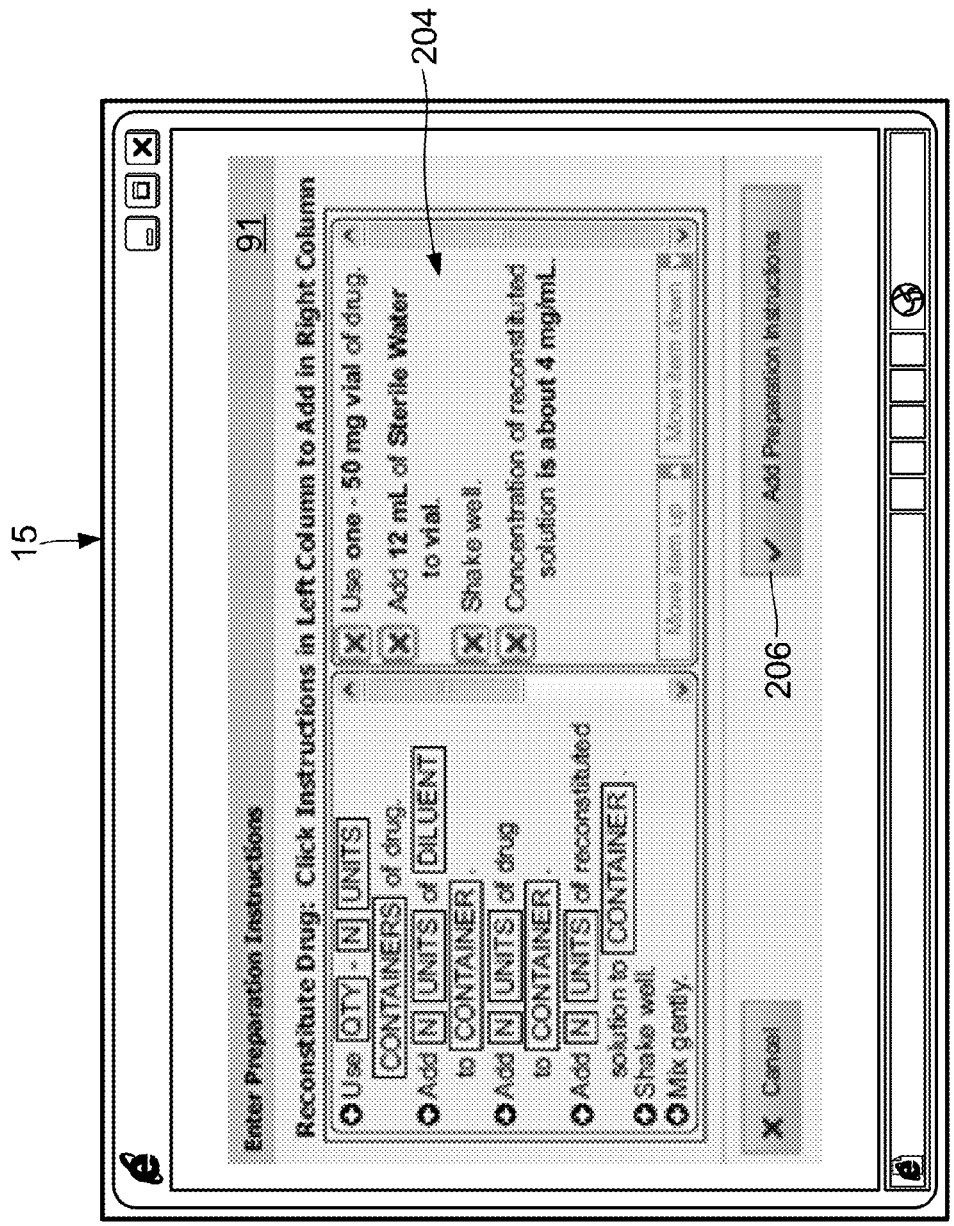
FIG. 23 shows an illustrative embodiment of an instruction summary in the Instruction Building interface.

Selecting the "Done" button inputs confirmation that the instructions for that preparation are complete, resulting in the preparation of an instruction summary 204 in the Instruction Building interface 91 as shown in FIG. 23. The steps appearing in the summary can optionally be deleted, and/or rearranged upward (to occur earlier in the process of creating the preparation) and/or downward (to occur later in the process of creating the preparation). Confirming the information in the summary 204 is accomplished by selection of the Add button 206, which also saves the instructions for that specific drug preparation in the corresponding entry in the formulary 36, which can then be updated over the communication network 40, or delivered to the computer terminal 10 via a portable computer-readable medium such as a USB flash drive, CD, etc. . . .

Figure 24:
FIG. 24 shows an illustrative embodiment of a label with label content including instructions for a preparation.

When a preparation for a drug is to be created as described herein, the desired preparation is entered into the computer terminal 10 by manual text entry, menu selection, scanning a barcode, transmitting the desired preparation over the communication network 40, etc. . . . Once the desired preparation has been received by the computer terminal 10, the computer terminal 10 can optionally display the instructions prepared by the pharmacist as described above. The instructions can be displayed by the display device 14 provided to the computer terminal 10 as shown in any of FIGS. 8, 10, 13, 15 and 16, for example. Further, any portion of the instructions can also be printed by the printer 26 as label content 34 onto the label 12, as shown in FIG. 24.

Examples of preparing drugs, include examples for instance of preparing a diluted drugs or reconstituted drugs, using the computer terminal 10 are provided for each of Drug A, Drug B and Drug C in FIG. 4, as follows:

A prescribing physician has prescribed a total dose and total volume of Drug A to be administered to a patient as shown in FIG. 6. The prescription 80 specifies the order ID 82, which can be thought of as a unique serial number assigned to the prescription for internal record keeping purposes, and the prescriber's ID 84 identifying who issued the prescription. Patient information 86 identifies the patient by at least one of: Patient Name; Patient ID; Date of Birth, who is to receive the prescribed drug. Drug information 88 identifies Drug A as the drug to be prepared, along with the desired total dose 54 and total volume 56 of Drug A to be administered. For the present example, a dilution of Drug A having a total dose and total volume of 100 mg/50 mL has been prescribed by the prescribing physician. Any special delivery instructions such as "IV", "Syringe Pump" and the delivery rate of "10 mg/hour" can also optionally be specified in the prescription 80. At least a portion, and optionally all of the above information can be encoded, or stored at a location identified by, or otherwise made available in response to scanning a machine-readable code such as the barcode 90. Scanning the barcode 90 with the reader 18 allows the computer terminal 10 to identify information indicative of the desired dilution, thereby minimizing the likelihood of human error in entering such information into the computer terminal 10.

In response to scanning the barcode 90 on the prescription 80, or the barcode 60 applied to, or otherwise associated with the originating container 50 storing Drug A using the reader 18, the computer terminal 10 presents the user with the Drug A interface 92 shown in FIG. 7 using display 14. For embodiments where the barcode 90 included as part of the prescription, the computer terminal 10 can optionally select a originating container 50 storing Drug A with a concentration appropriate for preparing the desired dilution called for by the prescription. The computer terminal 10 can optionally select the parental container 50 of Drug A with a concentration that most closely matches the diluted concentration corresponding to the total dose and total volume of the desired dilution. According to alternate embodiments, scanning the barcode 60 provided to the parental container 50 for Drug A, for example, inputs Drug A as the concentrated drug from which the dilution with the total dose 54 and total volume 56 specified in the prescription 80 is to be prepared. A summary 94 is presented identifying Drug A and the information related to that drug as stored in the originating container 50. The predefined preparations 68 from which the user can select the desired dilution called for by the prescription 80 are also presented by the display. The user preparing the dilution can touch an appropriate region of the Drug A interface 92 displayed by a touch-sensitive display 14 or manipulate a mouse or other computer pointing device to manually insert an "X" in the field 96 corresponding to the desired dilution called for by the prescription. According to alternate embodiments, the "X" can be auto-populated in the field 96 in response to scanning the barcode 90 (FIG. 6) encoding information indicative of the desired dilution included as part of the prescription 80. Similarly, the user can manually insert an "X" in the diluent field 98 corresponding to the appropriate diluent to be used in preparing the desired diluent specified by the prescription 80.

According to alternate embodiments, the prescription can be transmitted by, or on behalf of a prescribing physician electronically as a "e-script", or electronic prescription. Regardless of the method and form of the prescription, the information included in the prescription can be substantially the same.

Regardless of how the fields 96, 98 are selected, once the desired dilution and the appropriate diluent have been selected, the computer terminal 10 calculates the quantity of Drug A to be extracted from its originating container 50 and combined with the appropriate diluent to achieve the desired dilution. The results of the calculation can be displayed to the user in a Preparation Instructions interface 100 displayed by the display 14 as shown in FIG. 8. The Preparation Instructions interface 100 presents the user with the quantity 102 of Drug A from the originating container 50 to be combined with the quantity 104 of the selected diluent to produce the total volume 56 of the dilution called for by the prescription 80. Preparing the dilution according to the displayed instructions also ensures the total dose 54 required of the dilution is also achieved. For the example shown in FIG. 8, 5 mL of Drug A with a starting concentration of 20 mg/mL results in the total dose of 100 mg of Drug A required of the desired dilution. Similarly, combining the 5 mL of Drug A with the 45 mL of the appropriate diluent, as instructed, results in the total volume of 50 mL as required of the desired dilution.

Figure 9:
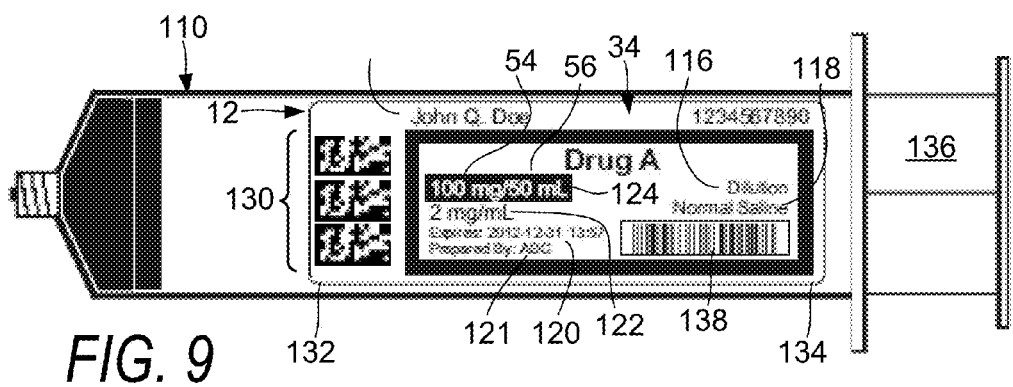
FIG. 9 shows an illustrative example of label content printed onto a label by a printer and applied to a delivery container in the form of a syringe.

The user can also input an instruction that causes the processing component 22 of the computer terminal 10 to transmit the label content 34 to be printed onto a label 12 to the printer 26. Such a label 12 printed by the printer 12 can optionally comply with a medical labeling standard governing at least one of a layout of label content 34, a color code utilized for the label 12, and mandated label content 34. According to alternate embodiments, the label 12 can optionally comply with a standard developed by a trade or professional organization, governing body, government agency, a healthcare provider or facility such as a hospital, or any other standards body setting forth policies for labeling drugs and dilutions. For example, FIG. 9 shows an illustrative example of label content printed onto a label 12 by the printer 26 and applied to a delivery container such as a syringe 110, for example.

The label content 34 printed by the printer 26 in response to receiving the print job from the processing component 22 can include at least one of: patient name 112, patient ID number 114, Drug ID 52, an indication 116 that a dilution is stored in the syringe 110, the diluent identity 118, an expiration date and/or time 120 of the dilution, information 121 indicative of the identity of the user who prepared the dilution, the dose and volume 54/56 of the dilution, and the concentration 122 of the dilution. Any portion, or all of this information can be recorded in a log entry to document the preparation of the dilution and the corresponding label 12. For the present example, a Non-standard pre-defined preparation 68 was selected and prepared by the user, so the label content 34 can also optionally include an indication 124 identifying the dilution as being a Non-standard pre-defined dilution. For example, the indication 124 includes the negative printing (e.g., color background with white text) of the total dose/total concentration 54/56.

At least a portion, and optionally all of the label content 34 can be encoded by a machine-readable code 130 that is also printed by the printer 26 on the label 12. The embodiment of the label content 34 in FIG. 9 shows three duplicate machine-readable codes 130, each encoding the same information for redundancy purposes. Each barcode 130 encodes information indicative of at least the patient, the drug and drug dilution. For the present embodiment, at least one of the barcodes 130 is arranged adjacent to a distal end 132 of the label 12, which is opposite a proximate 134 end of the label 12 that is positioned adjacent to a plunger 136 of the syringe 110 that is depressed into the syringe 110 to expel the dilution. Positioning at least one of the barcodes 130 adjacent to the distal end 132 of the label 12 helps to avoid a scenario where such barcode(s) 130 is/are blocked by a device that cooperates with a portion of the syringe 110 adjacent to the plunger 136, thereby avoiding obstructions of the barcode(s) 130 that would interfere with the reading of the barcode(s) 130. According to alternate embodiments, the user can specify, with the computer terminal 10, a label template establishing a desired layout defining the location of the barcode(s) 130 relative to the other label content 34. For example, a plurality of the barcodes 130 can all be arranged along the distal end 132 of the label 12 as shown in FIG. 9. Selecting a different label template can include the same information in the label content 34, but arrange the barcodes 130 or other label content at a different spatial location on the label 12 to meet the needs of the user.

Additionally, the present embodiment also includes a secondary barcode 138 or other machine-readable code. The secondary barcode 138, if present, can encode a less-comprehensive quantity of information than the barcode(s) 130. For example, the secondary barcode 138 can optionally encode any information utilized by, and optionally specific to (e.g., information not universally used in a standardized manner outside the healthcare facility—as opposed to the drug name, for example) the healthcare facility where the computer terminal is located 10. More detail examples of the information encoded by the secondary barcode 138 include, but are not limited to: the information encoded by the barcode 60 provided to the originating container 50 for Drug A, information for auditing the pharmacy inventory at the healthcare facility, any information that can be retrieved from or inserted into an electronic medical record for the patient who is to receive the dilution, and the like.

In the preceding example the user selected one of the pre-defined preparations 68 presented by the Drug A interface 92 shown in FIG. 7. However, there may be a need to prepare a dilution other than those included in the pre-defined preparations 68. To prepare such a dilution, and optionally a corresponding label 12, the user can insert the "X" mark in the field 140 corresponding to the "Other" option instead of the field 96. Instead of proceeding to the Preparation Instructions interface 100 shown in FIG. 8, the user is presented with the Other Dilution interface 142 shown in FIG. 10. As shown, the user is presented with a text entry field 144 in which the user can manually enter (e.g., freely type) the desired total dose of the dilution and another text entry field 146 in which the user can manually enter (e.g., freely type) the desired total volume of the dilution. The Other Dilution interface 142 also includes the summary 94 of the Drug to be diluted and includes the available diluents 148 from which the user can select the appropriate diluent to be used to prepare the dilution.

Figure 10:
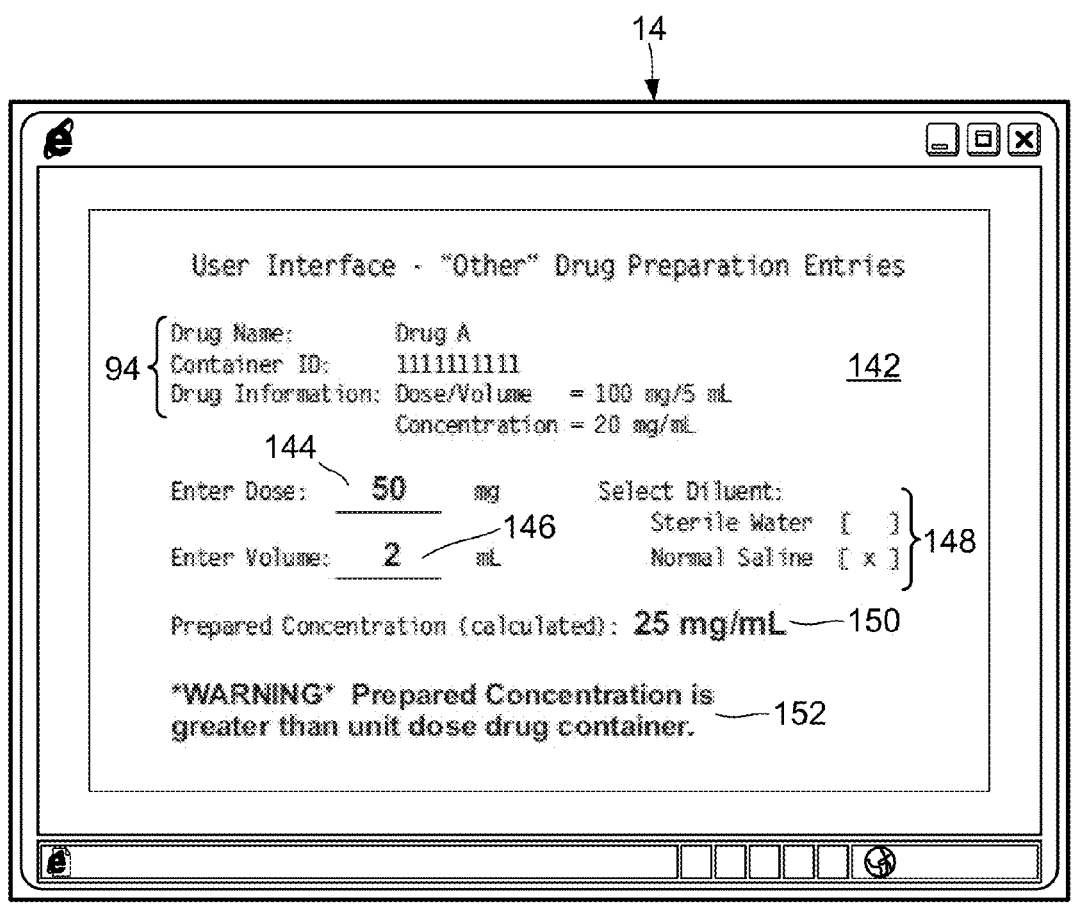
FIG. 10 shows an embodiment of an Other Dilution interface presenting a user with a text entry field in which the user can manually enter a desired total dose and a desired total volume of the dilution.

For the example in FIG. 10, the user has entered 50 mg as the desired total dose, and 2 mL as the desired total volume, apparently in error by omitting the zero from the numeral "20" the user desired to enter into the total volume field 146. The prepared concentration 150 of the dilution is calculated to be 25 mg/mL based on the values actually entered by the user. But since the concentration of Drug A in parental container 50 was originally only 20 mg/mL, it is not possible to dilute Drug A with a diluent to produce a dilution with a concentration greater than the starting concentration of 20 mg/mL. In other words, the user can not increase the concentration of Drug A by diluting it. Detecting such an outcome based on the user's erroneously-input entries, the computer terminal 10 presents the user with a warning 152 alerting the user to this condition and requiring correction before the process is permitted to proceed. The user can then correct the erroneous entry of the total volume by entering "20" into the total volume field 146 as shown in FIG. 11

According to alternate embodiments, the computer terminal 10 can also optionally determine when the user enters values in the total dose field 144 and total volume field 146 that would require precise measurements of Drug A or the diluent that cannot reasonably be expected of a human user. For instance, if the values entered by the user require the combination of 0.1 mL of diluent with a quantity of Drug A, the computer terminal 10 can issue another warning alerting the user to the fact that a 0.1 mL measurement of the diluent is impractical, and optionally suggesting starting the dilution process with another originating container 50 of Drug A having a lower-concentration.

Other embodiments of the dilution-preparation process utilizing the computer terminal 10 may require a multi-step dilution. For example, the prescription shown in FIG. 12 requires Drug B to be diluted to prepare a dilution with a dose and volume of 20 mg/20 mL. However, as shown in FIG. 4, Drug B is a powder stored in an originating container 50 with a total dose 54 of 50 mg. In response to reading the barcode 60 on the originating container 50 for Drug B with the reader 18, the user would select 20 mg/20 mL from the list of pre-defined preparations 68, if available, or request preparation of the field 140 corresponding to the "Other" option as described above with reference to FIG. 7. In response to selecting the field 140 corresponding to the "Other" option, the user would be prompted to enter the total dose and total volume of the desired dilution, in response to which the user would enter 20 mg as the total dose and 20 mL as the total volume into the Other Dilution interface 142 as describe above with reference to FIG. 11.

Figure 13:
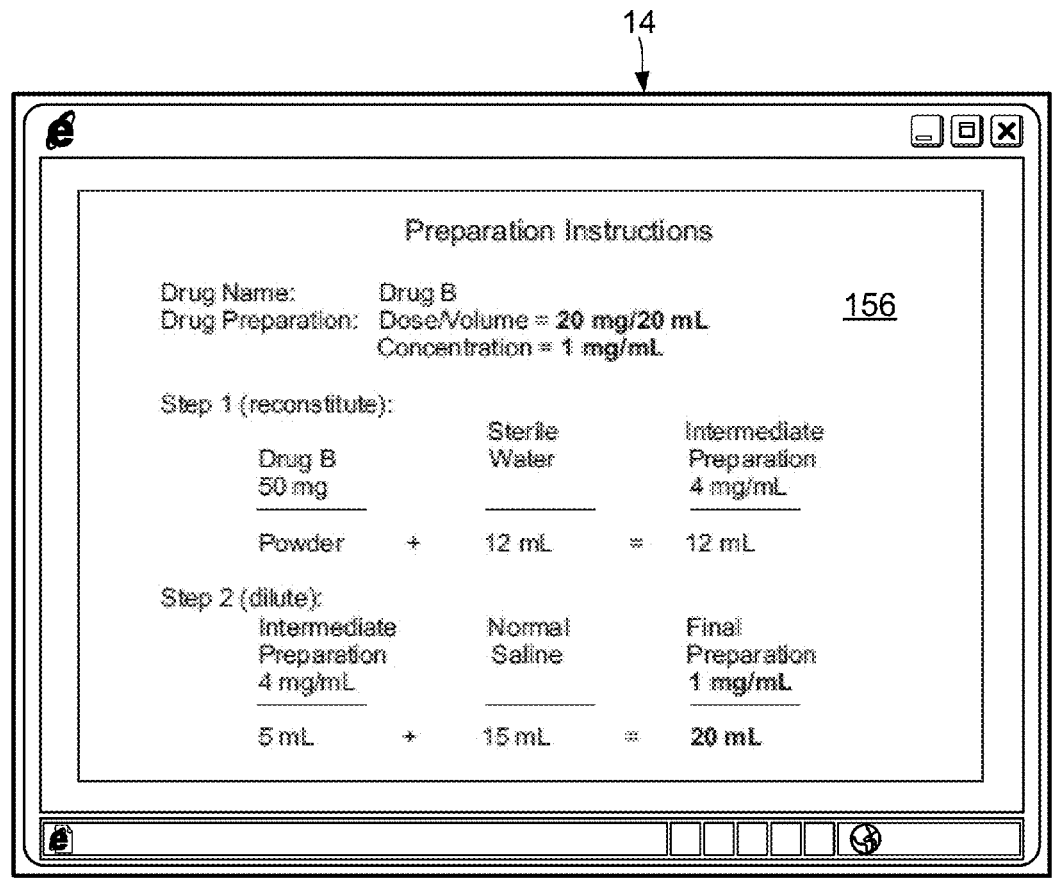
FIG. 13 shows another embodiment of a Preparation Instructions interface being displayed by a computer terminal.

Determining that the dilution requested by the user would require copious amounts of diluent, the processing component 22 of the computer terminal 10 transmits a signal resulting in the Preparation Instructions interface 156 being displayed by the display 14 as shown in FIG. 13. According to the present embodiment, the Preparation Instructions interface 156 instructs the user to prepare the dilution in a multi-step process. First, the user is to combine all 50 mg of Drug B in the originating vial 50 with 12 mL of water to produce an intermediate preparation of Drug B having a concentration of approximately 4 mg/mL and a total volume of approximately 12 mL. Although the exact concentration of Drug B in the intermediate preparation would be closer to 4.167 mg/mL, the computer terminal 10 can be configured to round to the nearest integer due to the imprecise nature of volumetric measurements.

In the second step, the user is to extract approximately 5 mL of the intermediate preparation and combine that quantity of the intermediate preparation with approximately 15 mL of Normal Saline as the diluent. The 5 mL of the intermediate preparation includes a total dose of approximately 20 mg of Drug B and, in combination with the 15 mL of the Normal Saline, results in a dilution with a total dose of 20 mg of Drug B in a total volume of about 20 mL, as desired.

Figure 14:
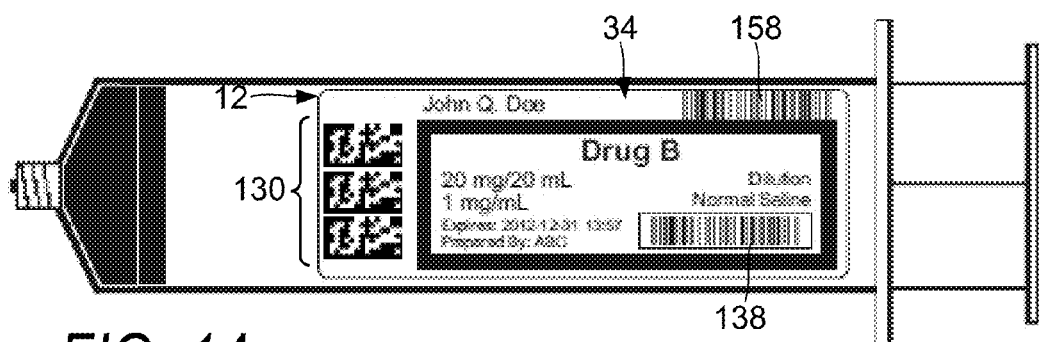
FIG. 14 shows an embodiment of a label bearing label content specific to a dilution of Drug B prescribed in FIG. 12 and corresponding to the instructions in FIG. 13.

With the dilution prepared the user can input the instruction to proceed with printing of the label 12 with the label content as shown in FIG. 14. The label content 34 in FIG. 14 is substantially the same as that in the embodiment appearing in FIG. 9, but specific to the dilution of Drug B discussed above. However, a tertiary barcode 158 encodes patient-specific data such as the name and/or patient ID number of the patient who is to receive the dilution of Drug B.

Although the computer terminal 10 instructed the user to dilute Drug B as a multi-step process due to the amount of diluent that would have been required of a single step dilution, other embodiments of the computer terminal can be adapted to instruct the user to perform a multi-step dilution in response to determination that a drug to be diluted is in short supply. For instance, the formulary 36 can optionally indicate that only a single originating container 50 of a drug at a first concentration remains in the pharmacy's inventory. In response to determining there is a limited supply of that drug at that starting concentration, the computer terminal 10 can be adapted to instruct the user to prepare a dilution of the drug in question starting with an originating container 50 having a second concentration that is greater than the first concentration, assuming an originating container 50 of the second concentration is available, and not in short supply (or at least more available in greater quantities than the originating container at the first concentration).

Another illustrative embodiment of a prescription requiring a dilution is shown in FIG. 15. Such prescriptions are commonly encountered when preparing dilutions to be administered during a surgical procedure or in an emergency situation, for example. As shown, the prescription 160 requires an unknown or unspecified quantity of Drug C diluted to a concentration of 0.25 mg/mL. The user can scan the barcode 60 provide to the originating container 50 of Drug C to commence the dilution preparation process. As shown in FIG. 5, drug entry C indicates that the corresponding drug is of a type that can be diluted to a desired concentration rather than a desired total dose and total volume as described above. For such drugs, scanning the barcode 60 provided to the originating container 50 for Drug C causes the computer terminal 10 to display the Preparation Instructions interface 164 shown in FIG. 16. As shown in the Preparation Instructions interface 164, the user is instructed to prepare a dilution by combining equal parts, by volume, of Drug C from the originating container 50 with a concentration of 0.5 mg/mL and Sterile Water. Thus, if 50 mL of Drug C at the desired concentration is desired, the user can combine 25 mL of Drug C having a concentration of 0.5 mg/mL with 25 mL of Sterile Water.

Figure 17:
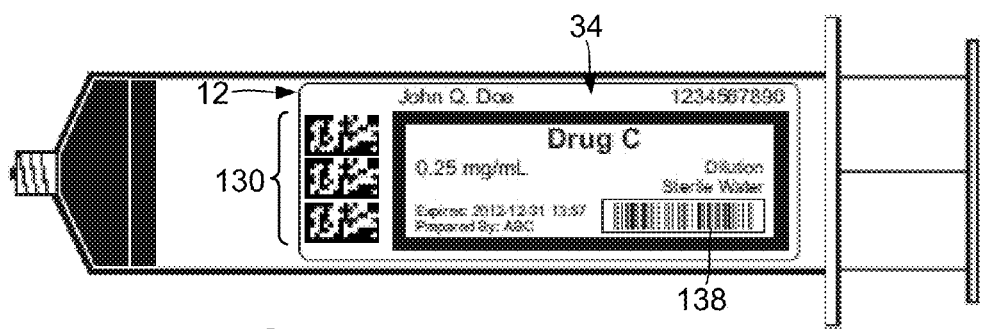
FIG. 17 shows an embodiment of a label bearing label content specific to a dilution of Drug C prescribed in FIG. 15 and corresponding to the instructions in FIG. 16.

FIG. 17 shows an illustrative embodiment of a label 12 for a dilution to a specific concentration prepared according to the instructions displayed in the Preparation Instructions interface 164 in FIG. 16. The label content 34 is generally analogous to that appearing in the labels of FIGS. 9 and 14, but only the concentration is included in the label content 34 rather than the total dose and total concentration as described above.

In another embodiment of the invention, part or all of the information contained in the preparation instructions can be included as part of the label content. For example, FIG. 9 shows label 12 for Drug A with diluent identity 118 consisting of Normal Saline. Referring back to the Preparation Instructions for Drug A in FIG. 8, the amount of Normal Saline used to prepare the drug is shown as 45 ml in quantity 104. This quantity information can be included as part of the label 12 shown in FIG. 9. The diluent quantity 104 with the diluent identity 118 can be included on the label to improve the information available to clinician administering the syringe. Similar to the previous example, the label can include information such as the specific dose and/or volume of the drug or drugs in the syringe, the amount and type of diluent used to reconstitute the drug or drug, and the amount and types of other diluents added to the syringe during the preparation process.

Illustrative embodiments have been described, hereinabove. It will be apparent to those skilled in the art that the above devices and methods may incorporate changes and modifications without departing from the general scope of this invention. It is intended to include all such modifications and alterations within the scope of the present invention. Furthermore, to the extent that the term "includes" is used in either the detailed description or the claims, such term is intended to be inclusive in a manner similar to the term "comprising" as "comprising" is interpreted when employed as a transitional word in a claim.

What is claimed is:

1. A system for presenting information related to a drug dilution, the system comprising:
a non-transitory, computer-readable memory storing a drug database comprising a plurality of drug entries, each of the plurality of drug entries comprising: (i) a drug identification that identifies a drug stored in a drug container, (ii) a concentration of the drug stored in the drug container; and (iii) a plurality of pre-defined dilution options that are selectable by a user to specify a desired dilution of a concentrated drug to be labeled, the pre-defined dilution options comprising at least one of a first option having a pre-defined total dose and/or a pre-defined total volume different from a corresponding value on the drug container, and a second option that is selectable to generate a label for a custom dilution that is not pre-defined;
a reader that is operable to read a first computer-readable code associated with the concentrated drug to be diluted and transmit a concentrate signal;
an input device that presents the user with a user interface for entering the desired dilution of the concentrated drug requested for administration to a patient;
a computer processor adapted to interpret the concentrate signal and identify the concentrated drug based on content included in the drug database; and
a printer for printing label content onto a label to be applied to a delivery container for administering the desired dilution to the patient, wherein at least one of the plurality of pre-defined dilution options is designated in the drug database as a non-standard dilution and the printer generates a label indicating the label is for the non-standard dilution.

2. The system of claim 1 further comprising a printer for printing label content onto a label to be applied to a delivery container storing the desired dilution to be administered to the patient, wherein the computer processor is further adapted to transmit a print signal instructing the printer to print a second computer-readable code encoding information identifying the concentrated drug, a diluent used to dilute the concentrated drug, and a total dose and total volume of the desired dilution as label content onto the label.

3. The system of claim 1, wherein the reader comprises a barcode reader.

4. The system of claim 1, wherein each of the plurality of drug entries comprises a total dose and a total volume of the drug in the drug container.

5. The system of claim 1, wherein the printer does not print the visible marking as part of the label content when another of the plurality of pre-defined dilutions, other than the non-standard dilution, is input as the desired dilution.

6. The system of claim 1, wherein each of the plurality of drug entries further comprises at least one pre-defined diluent that is selectable by the user via the user interface as a diluent to be used to dilute the concentrated drug to the desired dilution.

7. The system of claim 1, wherein the computer-readable memory stores, for each of the plurality of drug entries, a permission entry indicating whether dilution of the drug is permissible or required.

8. The system of claim 1, wherein the computer processor is further adapted to determine whether the desired dilution input by the user exceeds the concentration of the concentrated drug to be diluted, and transmit a warning signal warning the user that the desired dilution of the concentrated drug can not be achieved.

9. The system of claim 1, wherein the recipe comprises a volume of the concentrated drug and a volume of the diluent to be combined to achieve a total dose and total volume of the desired dilution.

10. A system for presenting information related to a drug dilution, the system comprising:
- a non-transitory, computer-readable memory storing a drug database comprising a plurality of drug entries, each of the plurality of drug entries comprising: (i) a drug identification that identifies a drug stored in a drug container, (ii) a concentration of the drug stored in the drug container; and (iii) a plurality of pre-defined dilution options that are selectable by a user to enter a desired dilution of a concentrated drug to be labeled, the pre-defined dilution options comprising at least one of a first option having a pre-defined total dose and/or a pre-defined total volume different from a corresponding value on the drug container, and a second option that is selectable to generate a label for a custom dilution that is not pre-defined;
- a reader that reads a first computer-readable code associated with the concentrated drug to be diluted and transmits a concentrate signal;
- an input device that presents the user with a user interface for entering the desired dilution of the concentrated drug requested for administration to a patient;
- a computer processor that is adapted to interpret the concentrate signal, identify the concentrated drug based on content included in the drug database and determine label content to be printed onto a label that is to be applied to a delivery container for administering the desired dilution to the patient, wherein the label content comprises a second computer-readable code encoding information identifying the desired dilution and a total dose and total volume of the desired dilution; and
- a printer that prints label content onto a label for a delivery container for administering the desired dilution to the patient, wherein at least one of the plurality of pre-defined dilution options is designated in the drug database as a non-standard dilution and the printer generates a label indicating the label is for the non-standard dilution.

11. The system of claim 10, wherein the printer does not print the visible marking as part of the label content when another of the plurality of pre-defined dilutions, other than the non-standard dilution, is input as the desired dilution.

12. The system of claim 10, wherein the computer-readable memory stores, for each of the plurality of drug entries, at least one pre-defined diluent that is selectable by the user via the user interface as a diluent to be used to dilute the concentrated drug to the desired dilution.

13. The system of claim 10, wherein the computer-readable memory stores, for each of the plurality of drug entries, a permission entry indicating whether dilution of the drug is permissible or required.

* * * * *